United States Patent [19]

Brenner

[11] Patent Number: 5,436,165
[45] Date of Patent: Jul. 25, 1995

[54] REACTION CONTROL AND SOLIDS CHARACTERIZATION DEVICE

[76] Inventor: Alan Brenner, 679 Westchester, Grosse Point Park, Mich. 48230

[21] Appl. No.: 937,857

[22] PCT Filed: Apr. 17, 1991

[86] PCT No.: PCT/US91/02614

§ 371 Date: Dec. 17, 1992

§ 102(e) Date: Dec. 17, 1992

Related U.S. Application Data

[63] Continuation-in-part of Ser. No. 510,505, Apr. 17, 1990, Pat. No. 5,342,580.

[51] Int. Cl.$^6$ ............... G01N 25/18; G01N 27/18
[52] U.S. Cl. ............................ 436/149; 422/90; 422/95
[58] Field of Search ............ 422/68.1, 69, 83, 88, 422/90, 92, 93, 95, 98; 436/34, 37, 149; 73/73, 74, 75, 23.4, 23.42, 25.03, 25.05

[56] References Cited

U.S. PATENT DOCUMENTS

| | | | |
|---|---|---|---|
| 1,981,172 | 11/1934 | Harrison | 422/95 X |
| 2,753,246 | 7/1956 | Shields et al. | 436/37 |
| 3,059,478 | 10/1962 | Coggeshall et al. | 73/38 X |
| 3,211,006 | 10/1965 | Haley | 73/865.5 |
| 3,211,007 | 10/1965 | Atkins | 73/865.5 |
| 3,304,170 | 2/1967 | Hinsvark | 73/25.03 |
| 3,349,625 | 10/1967 | Benusa et al. | 73/865.5 |
| 3,585,861 | 6/1969 | Keng | 73/865.5 |
| 3,589,172 | 6/1971 | Bowman | 73/25.03 |
| 3,732,736 | 5/1973 | Glaude et al. | 73/865.5 |
| 3,850,040 | 11/1974 | Orr et al. | 73/865.5 |
| 3,922,904 | 12/1975 | Williams | 73/19.1 |
| 4,164,862 | 8/1979 | Jackson | 73/25.03 |
| 4,359,891 | 11/1982 | Ahlstrom et al. | 422/89 X |
| 4,489,593 | 12/1984 | Pieters et al. | 73/38 |
| 4,496,249 | 1/1985 | Lee et al. | 436/37 X |
| 4,515,751 | 5/1985 | Krieg | 422/88 X |
| 4,528,850 | 7/1985 | Witier | 73/865.5 |
| 4,566,326 | 1/1986 | Lowell | 73/865.5 |
| 4,594,879 | 6/1986 | Maeda et al. | 73/25.03 X |
| 4,626,412 | 12/1986 | Ebner et al. | 422/78 X |
| 4,762,010 | 8/1988 | Borghard et al. | 73/865.5 |
| 4,838,706 | 6/1989 | Coey et al. | 73/19.1 X |
| 4,856,320 | 8/1989 | Bose et al. | 73/30.01 |
| 4,865,996 | 9/1989 | Castleman et al. | 422/89 X |
| 4,944,035 | 7/1990 | Aagardl et al. | 73/25.03 X |
| 4,967,591 | 11/1990 | Rougufrol et al. | 73/38 |
| 4,972,730 | 11/1990 | Camp et al. | 73/865.5 |
| 5,009,849 | 4/1991 | Ebner et al. | 436/34 X |
| 5,016,468 | 5/1991 | Jennings | 73/73 |
| 5,039,489 | 8/1991 | Gleaves et al. | 436/159 |
| 5,058,442 | 10/1991 | Yamanaka et al. | 73/865.5 |
| 5,109,716 | 5/1992 | Ito et al. | 73/865.5 |
| 5,157,960 | 10/1992 | Brehm et al. | 73/38 |

FOREIGN PATENT DOCUMENTS 127514 12/1984 European Pat. Off. .

OTHER PUBLICATIONS

A. Jones, et al., Temperature–Programmed Reduction for Solid Materials Characterization, Marcel Dekker, Inc., vols. 23–25, pp. 68–79.

(List continued on next page.)

*Primary Examiner*—Robert J. Warden
*Assistant Examiner*—Robert Carpenter
*Attorney, Agent, or Firm*—Pollock, Vande Sande & Priddy

[57] ABSTRACT

An apparatus and method for measuring the amount of gas adsorbed on or desorbed from a solid and for analyzing and surveying reactions of a gas with a solid are disclosed. Reactions can be of either a physical or chemical nature. Parameters of governing comprise a broad range of pressure, temperature, and the rate of gas flow. More particularly, the invention provides an apparatus and method for very accurate and rapid measurement of the amount of gas adsorbed on or desorbed from a solid and means to govern the reaction of a gas with a solid at pressures from high vacuum to high pressure.

9 Claims, 12 Drawing Sheets

OTHER PUBLICATIONS

E. Petersen, et al., Catalyst Deactivation, Marcel Dekker, Inc., vols. 23–30, pp. 99–123.

H. Boer, et al., Automatic Apparatus for Catalyst Characterization by Temperature-Programmed Reduction/Desorption/Oxidation, Rev. Sci. Instrum. 53(3), Mar. 1982, pp. 349–361.

W. Blakely, et al., New Instrumentation and Techniques to Monitor Chemical Surface Reactions on Single Crystals Over A Wide Pressure Range ($10^{-8}-10^5$ Torr) in the Same Apparatus, J. Vac. Sci. Technol., vol. 13, No. 5, Sep./Oct. 1976, pp. 1091–1096.

The CDS 900 Bench-Scale Reaction System—Chemical Data Systems, Inc., 1987.

Series 4570 High Pressure/High Temperature Reactor—Stirred Reactors—Parr Instrument Co., pp. 43–47.

ChemiSorb 2800—Micromeritics (3 pages).

Autosorb-6—Automatic Volumetric Sorption Analyzer, Quantachrome Corp. (6 pages).

Catalyst Characterization—Computer-Controlled Temperature Programmed Systems—Altamira Instruments, Inc. (2 pages).

Vidal, et al., Measurement of Physical Adsorption of Gases at High Pressure, Rev. Sci. Instrum. 61(4), Apr. 1990, pp. 1314–1318.

Jones, et al., Temperature-Programmed Reduction for Solid Materials Characterization, Marcel Dekker, Inc. (1986), pp. 68–73.

Abstract of Japan, vol. 15, No. 218 (P-1210) 4 Jun. 1991.

Abstract of Japan, JP-A-30 61 884 (Idemitsu Kosan Co. ltd.) 18 Mar. 1991.

REACTION CONTROL AND SOLIDS CHARACTERIZATION DEVICE

CROSS-REFERENCE TO RELATED APPLICATIONS

This is a continuation-in-part of my copending U.S. applicaton Ser. No. 07/510,505 entitled, "Reaction Control Device," filed on Apr. 17, 1990, now U.S. Pat. No. 5,342,580.

SPECIFICATIONS

The invention relates generally to an apparatus and method for measuring the amount of gas adsorbed on or desorbed from a solid. More particularly, the invention relates to an apparatus and method that will also provide a governing of the reactions of a gas with a solid by pressure and by temperature and by rate of flow in a broad range of those parameters. Most particularly, the invention provides an apparatus and method for very accurate and rapid measurement of the amount of gas adsorbed on or desorbed from a solid and means to govern the reaction of a gas with a solid at pressures ranging from substantially below one atmosphere to substantially above One atmosphere.

BACKGROUND OF THE INVENTION

It is estimated that solid catalysts account for about 90% of manufactured chemicals, and thus are extremely important to the chemical industry. It is well known that the performance of a catalyst can be greatly altered by small changes in its properties. Therefore, measuring the rate and products of chemical reactions between gases and catalysts and the characterization of catalysts ,are important endeavors. The most common and important methods of characterizing a solid catalyst involve the measurement of the adsorption of a gas on and the desorption of a gas from a catalyst.

It is also important to characterize many other types of noncatalytic solids by measuring their interaction with a gas. One such method is to determine the pore structure of a solid by measuring the physical adsorption of a gas near its boiling point, this frequently being done with $N_2(g)$ near 77K. For example, the weathering of concrete is influenced by it pore structure. Another example is to determine the strength or quantity of acidic sites on the surface of a solid polymer by measuring the adsorption of a base, such as $NH_3(g)$.

Reactivity measurements of a catalyst are almost always done at pressures at or above 1 atm, and it is common for such measurements to be done at pressures exceeding 10 atm. In contrast, some of the most important methods of characterizing a solid require measuring the adsorption and desorption of a gas at pressures substantially below 1 atm. One of the most accurate and important of these techniques is termed the volumetric method and requires high vacuum capability ($P < 5 \times 10^{-5}$ torr, 760 torr = 1 atm) and a highly accurate pressure transducer for the range of about 0 to 760 torr.

The measurement of reactivity typically involves exposing a catalyst to a reaction mixture and measuring the amount and type of products formed. This data yields the activity and product distribution of a catalyst at the given reaction conditions. It is normally desirable to control the rate of flow, temperature, and pressure of reactants in a reactor. By varying these parameters, information can also be obtained on the kinetics of a reaction including the rate constant, activation energy, and orders of the reaction.

Reactors operable at high pressure are made of metal. Since metal is strong, virtually all such reactorrs are rated at > 1000 psia (14.7 psia = 1 atm). Pressurized containers pose an explosion hazard. They are not combined with good vacuum capability and the volume of the reactor is usually not critical. Virtually all manufactured laboratory scale reactors usuable at high pressure have a volume in the range of 100 mL to 10 L.

A high pressure reaction system will have a high pressure gauge. Since such an apparatus is not designed for measuring the adsorption and desorption of a gas with a solid by the volumetric method, there is no need for also having a highly accurate low pressure gauge. The most accurate high pressure gauges have an accuracy of about 0.1% of full scale, but in the lower end of their range are much less accurate due to noise and drift. Therefore, such a gauge with a range of 1000 psia can measure a pressure to an accuracy of only about 53 torr. Assuming a very small reaction volume of 100 mL and a temperature of 20° C., this corresponds to an error in measuring the amount of gas present of 6.5 mL STP (STP = standard temperature and pressure). Due to the specific experimental steps required when measuring the adsorption and desorption of a gas with a solid by the volumetric method, the repeatability of a gauge is a more meaningful parameter than the accuracy of a gauge for calculating the accuracy of the amount of gas adsorbed on or desorbed from a solid. However, in some cases manufacturers do not give a repeatability specification. A rough value is for the repeatability to be 3-fold better than the accuracy. In this case, the previously described apparatus could be used to measure the amount of adsorption or desorption to an accuracy of about 2.2 mL. This is about 59-fold larger than is acceptable for the least accurate apparatus for measuring the amount of gas adsorbed on or desorbed from a solid utilizing the volumetric method.

The most common and important methods of measuring the interaction of a gas with a solid are to measure the adsorption and desorption of a gas with a solid. Especially important is the measurement of the amount of equilibrium physical or chemical adsorption or desorption of a gas with a solid as a function of pressure. Physical adsorption and desorption data enable the determination of important properties of a solid including its surface area and pore structure. Chemical adsorption and desorption data enable the determination of a variety of properties of a solid including the dispersion and average crystallite size of a supported metal, the number and strength of acidic and basic sites on a solid, the energetics of adsorption and desorption, and the number of catalytically active sites on a solid.

There are two main techniques of doing these measurements: the volumetric method and the flowing gas technique The volumetric method is easily the most accurate, informative, and widely applicable. For both methods there is virtually no limit on the specific (per gram) or total surface area of a solid sample. In particular, samples of specific surface area from 0.01 to 1500 $m^2/g$ can be used.

In the volumetric method a dose of gas at an accurately known pressure and temperature is expanded from a dosing volume of accurately known size into a reactor containing a sample at constant temperature, Gas laws enable the calculation of the quantity of gas contained in the dosing volume. Initially He gas is used as the dosing gas, and this enables an accurate determination of the pressure drop caused by the expansion of a nonadsorbing gas, The reactor and dosing volume are then evacuated and the process repeated with an adsorbate. By accurately measuring the gas pressure before and after the valve is opened, it is possible to accurately calculate the amount gas which is adsorbed on the solid. A permutation of this technique enables the desorption of a gas to be measured.

Since the calculations of gas adsorbed or desorbed involve gas laws, the accuracy and sensitivity of the data are inversely proportional to the sum of the volumes of the reactor plus dosing region plus pressure transducer. For this reason this total volume is kept small, a typical value being 30 mL.

The data are highly sensitive to leaks and outgassing of the apparatus and any residual contamination. Especially if the solid being investigated is a catalyst, the sensitivity to such spurious effects can be great, with the exposure to 0.001 mL STP of contaminant over the lifetime of the measurement (roughly 1 h) sufficient to alter the results in some cases. A scratch or other inadvertent channel to the atmosphere 0.5 cm long by only $2 \times 10^{-4}$ cm diameter is sufficient to cause such a leak. Therefore, great attention to details of construction and operation of such an apparatus is required. Standard methods of vacuum technology can result in a system with low leak and outgassing. Residual gases are quickly removed by evacuation. When the measurements are of physical adsorption or desorption, it is common practice to use a mechanical vacuum pump capable of achieving a vacuum of about $10^{-3}$ torr. If chemical adsorption or desorption is being measured, which is generally much smaller in amount and much mere sensitive to contamination and leaks, it is common practice to use a high vacuum pump capable of achieving a vacuum of at least $10^{-5}$ torr.

Due to the unreactive surface which they provide, glass vessels are often used for reactions in the low pressure regime, but are not suitable for reactions at high pressure. Evacuated glass containers pose an implosion hazard.

The measurement of adsorption or desorption of a gas with a solid by the volumetric technique also requires a yew accurate pressure gauge. The accuracy of the results strongly depend on the accuracy of the pressure gauge. The large majority of measurements are made in the pressure range of 0 to 300 torr, but sometimes pressures near 1 atm are used. Therefore, it is common practice to utilize a pressure gauge which reads to about 1000 torr. A mediocre gauge for this type of apparatus and pressure range has an accuracy of about 0.3% of full scale. Gauges of this and much higher accuracy which have full scale ranges of 1 to 1000 torr are readily available. The mediocre gauge can measure a pressure with an accuracy of 3 torr. Assuming a typical reaction volume of 30 mL for an apparatus designed for such measurements and a temperature of 20° C., this corresponds to an error in measuring the amount of gas present of 0.11 mL STP. As noted previously, this results in an error for measuring the amount of adsorption or desorption of about 0.04 mL STP. Apparatus which are of substantially lower accuracy are not operable to meaningfully measure the adsorption or desorption of a gas with a solid by the volumetric technique.

It is sometimes desirable to measure the amount of adsorption at a low equilibrium pressure utilizing the volumetric method. This is easy with manually operated valves, since the operator can throttle the gas flow. However, in a computer controlled apparatus using remotely actuated valves this becomes difficult. A typical time for a remotely controlled packless valve to close is about 0.5 s. If the dosing volume is initially evacuated, then opening a valve to a gas source will cause a gas burst before the valve can be closed. This is especially a problem in a multifunctional apparatus since the gas flow can not be restricted to a very low value. Further, in a well designed apparatus evacuation at pressures above 0.1 torr will be so fast that the pressure also can not be readily set by reducing a higher pressure. An error in setting the pressure of 1 torr at a pressure of 100 torr is inconsequential for adsorption measurements, but is not acceptable if the pressure of the gas in the dosing volume is to be less than about 10 torr.

Accordingly, it is also an object of this invention to provide improved means for setting low pressures in the dosing volume used for measuring the adsorption of a gas on a solid by the volumetric method.

The most common method of obtaining the amount of chemisorption of a gas on a solid by the volumetric technique is here termed the dual isotherm method. A number of data points is obtained of the adsorption as a function of pressure, here termed the first isotherm. The sample is then evacuated and the process repeated to obtain the second isotherm. In some cases each isotherm is fit to a straight line and the chemisorption is defined as the value of line 1 minus line 2 at zero pressure. Another treatment of the isotherms is to fit each isotherm to a curve, as by using linear regression analysis, and then define the chemisorption as a function of pressure as curve 1 minus curve 2. This method has the advantage of providing more information, but there is no general analytic function for fitting the two isotherms, so the chemisorption curve has error from the curve fitting of the two Isotherms. Because a good curve fit is important, it is also necessary to take a number of data points and this increases the time of the experiment. It would therefore be of great value to increase the speed of obtaining data for the dual isotherm volumetric method and also to be able to lower the effect of curve fitting error.

Curvature in the isotherms is most pronounced at low pressures and contains information on the energetics of adsorption. This data makes curve fitting more subject to error. Sometimes it is preferred to use data at higher pressures to calculate the amount of chemisorption. It would be desirable to be able to acquire data over a large pressure range but be able to select only some 0f the data to be used for calculating the chemisorption. It is also desirable to have a means of assessing the effects of experimental data and parameters (such as the dosing volume and sample weight) on the results.

Careful analysis of the errors in obtaining chemisorption data by the dual isotherm method yields the surprising result that for a well designed machine the experimental error is usually much less than the curve fitting error. By incorporating this unexpected result into the methodology of data acquisition and treatment, substantial increase in the accuracy and a decrease in the time of obtaining chemisorption data can be achieved.

Numerous devices are available to control the reaction of gases with solids at pressures $\geq 1$ atm. One prior art device is the model CDS 900 bench scale reactor system made by Chemical Data Systems, a division of Autoclave Engineers, Inc. of Oxford, Pa. This apparatus is capable of monitoring catalytic reactions at pressures between 1 atm and 1500 psia. A sample can be heated at temperatures up to 540° C. Heating and cooling of the reactor are relatively slow. Parr Instrument Company of Moline, Ill., manufactures a model 4570 stirred reactor which will operate from 1 atm to 5000 psia. A sample can be heated at temperatures up to 500° C. Heating and cooling of this reactor are also relatively slow. Parr and Autoclave Engineers manufacture a number of other devices which operate in the high pressure regime, but none which operate in the low pressure regime.

It is sometimes desirable to evacuate a high pressure reactor. This is done with a mechanical pump. A mechanical pump can reduce the pressure to about 0.01 torr in a reasonable amount of time which results in the removal of 99.999% of the gas in the reactor. Since such apparatus are not designed for measuring the adsorption and desorption of a gas with a solid by the volumetric method, there is no need for also having a high vacuum pump and all of its required gauges, flow paths, and peripheral valves. Whereas high pressure reaction equipment is necessarily robust, high vacuum equipment is relatively easily damaged. Furthermore, as will be described in a following section, due to the fact that the tubing in the high pressure system is of small diameter but large diameter tubing is required for useful operation of a high vacuum pump, even attaching such a pump would not result in achieving high vacuum in an acceptable amount of time. Therefore, the aforementioned prior art can not be readily modified to operate at high vacuum.

Reactors used at high pressures am constructed of metal which has a high thermal conductivity. Therefore, they are also not suitable for immersion in liquid $N_2$ which is the standard temperature for most measurements of the physical adsorption or desorption of a gas with a solid.

Consequently, there is no prior art apparatus which is capable of operating in the high pressure regime in a manner suitable for running chemical reactions and which can also operate in the low pressure regime in a manner suitable for accurately measuring the adsorption or desorption of a gas with a solid by the volumetric method.

Numerous devices are available to measure the adsorption and desorption of gases with solids at low and ambient pressure regimes by the volumetric method. A prior art device is the model Chemisorb 2800 device made by Micromeritics of Norcross, Ga. This apparatus is capable of monitoring the chemical adsorption of a gas on a solid catalyst in the pressure range of about 1000 to $10^{-3}$ torr. Pretreatment of a sample can be done at pressures down to $10^{-5}$ torr and temperatures up to 750° C. Thorough evacuation of a solid sample is a standard procedure when pretreating a solid prior to measuring the adsorption of a gas on it, and several additional evacuations are also required as part of the adsorption measurement. Evacuation of a solid contained in a sample holder and mounted on a Chemisorb 2800 is relatively slow. In practice, it is found that it takes about 30 to 60 min to reduce the pressure from 1 atm to $1 \times 10^{-5}$ torr. Exclusive of the evacuation time, a measurement of the chemisorption of a gas on a solid takes about 1 h. Thus, the time for the evacuations substantially increases the total time of an adsorption measurement. Heating rates of the Chemisorb 2800 are about 10° C./min, and it takes about 1 h to cool a reactor from 650 to 35° C.

Quantachrome of Syosett, N.Y., manufactures a model Autosorb 6 which measures the physical adsorption of $N_2$ gas at $-196°$ C. on a solid in the pressure range of about 0.1 torr to 1 Pretreatment of a sample can be done at pressures down to $10^{-3}$ torr and temperatures up to 450° C. Micromeritics and Quantachrome manufacture a number of other devices which operate at low or ambient pressure for the purpose of monitoring the adsorption or desorption of a gas with a solid, but none which operate at high pressure.

U.S. Pat. No. 4,489,593 issued in 1984 to Pieters and assigned to Omicron Technology Corporation of Berkeley Heights, N.J., is entitled "METHOD AND APPARATUS FOR DETERMINING THE AMOUNT OF GAS ADSORBED OR DESORBED FROM A SOLID". The apparatus claimed therein is exemplified by the model 100 manufactured by Omicron. This apparatus measures the physical adsorption and desorption of a gas with a solid in the pressure range of about 1000 to $1 \times 10^{-3}$ torr by measuring the pressure differential in a dynamic and volumetric manner as gas is continuously added to or withdrawn from the sample chamber. The apparatus can achieve an ultimate vacuum of about $10^{-7}$ torr and a solid sample can be heated to about 450° C. This and other apparatus for measuring the adsorption and desorption of gases which are manufactured by Omicron are inoperable at pressures above 1000 torr.

The pore structure distribution of a solid is commonly measured by the volumetric method. In this method the amount of gas physically adsorbed on or desorbed from a solid near the boiling point of the gas is measured over a range of pressures, commonly about 0.1 to 760 torr. The experimental methods and apparatus can be the same as used for measuring the surface area of a solid. The distinction lies in the requirement to acquire more data points and using a different mathematical treatment of the data for pore structure determination. Machines for determining the pore structure of a solid are made by several companies, including Micromeritics and Omicron. None of the prior art machines is capable of operating at pressures above 1000 torr, nor has the necessary flow controls for performing chemical reactions utilizing a flow of more than one gas.

Catalysts are often affected by exposure to air and require in situ pretreatments which often take as long as obtaining the desired experimental measurement. A sample can not be introduced to any of the aforementioned prior art apparatus without first exposing the sample to air. Therefore, if a sample is pretreated on one apparatus, there is both the inefficiency of transferring the sample to the second apparatus as well as having to repeat the pretreatment on the second apparatus.

Accordingly, it is an object of this invention to provide an apparatus which can accurately measure the reaction, adsorption, and desorption of a gas with a solid in a pressure range extending from well below to well above 1 atm. It is further an object of this invention to provide relatively fast rates of evacuation and a very low ultimate vacuum in the range of $10^{-9}$ torr. It is an object of this invention to protect the low pressure components of the apparatus from damage when the apparatus contains a gas at high pressure and to provide for safe operation. It is an object of this invention that chemical reactions performed at high pressures and adsorption or desorption measurements performed at low pressures can be done on a single sample without removing the sample from the apparatus or exposing it to air.

A second and less accurate and less widely applicable technique of measuring the equilibrium amount of adsorption or desorption of a gas with a solid is defined as the flowing gas technique. This method consists of passing a constant flow of gas over a solid sample at essentially constant temperature while a detector more or less continuously analyzes some parameter of the effluent gas in order to measure the disappearance of a component of the gas flow due to adsorption on the sample or the appearance of a component in the gas flow due to desorption from the sample. More particularly, the analyzer detects the adsorption or desorption of a gas with the solid by more or less continuously monitoring the concentration of the reactant gas which is contained in a large excess of an unreactive carrier gas. The detector is commonly a thermal conductivity detector (TCD) and the gas flow is almost always at ambient pressure. Some of the analyzers, including a TCD, are capable of operating at high pressures.

Some important properties of solids, such as the pore size distribution, can not be measured by this technique. This technique is also very limited in its ability to measure the amount of adsorption or desorption of a gas with a solid as a function of pressure. The main advantage of this technique is that the requisite apparatus is cheaper than for the volumetric technique, primarily because vacuum capability is not required.

A generalization of the* flowing gas technique involves changing the temperature of the sample at a known and normally constant rate while the analysis is being performed. This method is commonly referred to and is here defined as temperature programmed characterization (TPC). These measurements include temperature programmed desorption, reaction, decomposition, reduction and oxidation. In virtually all cases the temperature increases during the measurement. However, temperature programmed adsorption requires that the temperature be reduced in a controlled manner which is relatively difficult and this method is very rarely reported in the literature. This method can provide information on the energetics of adsorption. None of the aforementioned prior art apparatus can perform temperature programmed adsorption.

The flowing gas technique requires a small system volume. The amount of undesirable band spreading of an adsorption or desorption peak in the gas stream is proportional to the volume of the reactor plus, analyzer plus interconnecting tubing. Also, the response time of the technique increases linearly with this volume. For these reasons this volume is kept mall, a typical value being about 10 mL.

Control of leaks, outgassing, and contaminants is much harder in this type of system since vacuum technology is not normally used. In contrast to the case for systems which use the volumetric technique, no manufacturer of this type of equipment gives specifications for the degree of leak tightness or contamination of the apparatus. It is a common misconception that a leak from the atmosphere into an apparatus will not occur if the apparatus is at a pressure of ambient or above. In fact, inboard leaks through a sufficiently narrow channel occur at a rate independent of the internal pressure of an apparatus. As previously described, such leaks can seriously effect a measurement.

None of the prior art devices previously described can properly perform TPC. For example, the CDS 900 does not provide the necessary analyzer and flow path for the reactor effluent and the large volume in the apparatus would distort the data and diminish the sensitivity and accuracy of a measurement. The Chemisorb 2800 also does not have a suitable gas analyzer.

An example of an apparatus capable of TPC measurements is the AMI-1 manufactured by Altamira Instruments, Inc. of Pittsburgh, Pa. The AMI-1 uses a TCD. The AMI-1 is designed to flow gas through a single glass reactor in the flow range of 5 to 80 mL/min at a maximum temperature of 1100° C. and maximum heating rate of 40° C./min. The apparatus can not do TPC at subambient temperatures. The temperature of a solid sample can not be cooled at a known and constant rate so temperature programmed adsorption can not be performed with this apparatus. No ,,specification is given for the rate of cooling of the furnace. The AMI-1 is only operable near ambient pressure and has neither vacuum nor high pressure capability.

In a recent review of experimental methods and instrumentation for TPC (Alan Jones and Brian D.McNicol, Temperature-Programmed Reduction for Solid Materials Characterization, M. Dekker, Inc., N.Y., 1986, chapter 3) it is stated that all current apparatus only operate at ambient or subambient pressures, and the use of such a device at high pressure would be of great technical value. Another recent description of some TPC apparatus is provided by Menon (Catalyst Deactivation, Marcel Dekker, Inc. 1988, p. 99). H. Boer et. al. (Rev. Sci. Instrum. 53, 349 (1982)) described one of the very few apparatus which can perform temperature controlled adsorption. None of the apparatus described can also measure the amount of gas adsorbed on or desorbed from a solid sample by the volumetric method.

The AMI-1 has a gas sampling valve which can be used to pass pulses of a gas over a sample. This enables some measurements to be made of the amount of adsorption of gas by using a TCD to monitor the disappearance of gas from the pulse. However, in most cases the data obtained is less accurate then obtained with the volumetric method and the amount of equilibrium adsorption as a function of pressure can not be measured.

The most common detector used for TPC is a TCD. There are very few manufacturers of TCD's, the main source in the U.S. being Gow-Mac Instrument Co. of Bridgewater, N.J. The manufacturer specifies a maximum current at which a TCD can be operated. The value depends on type of gas flowing through the TCD and the temperature of the TCD. Higher currents increase the sensitivity of a TCD, but cause it to burn out quicker.

Prior to the start of TPC, it is necessary to stabilize the detector, usually a TCD. This delay time is here defined as the equilibration time. The equilibration time is primarily due to self heating of the TCD and the time necessary to achieve a pure flow of reactant gas through the TCD. The thermal equilibration time is about 1 h. In order to remove residual gas when the composition of the flowing gas is changed, it is common practice to purge the flow lines for an extended time. The time necessary to purge the lines increases as their volume increases and is also substantially increased by any volume within the lines which is not directly swept by the flowing gas. Virtually all valves contain some nonswept volume, and this is especially true of packless valves which are the valves having the lowest leak rate. A time of about 1 h is required to thoroughly purge a system. Since the time to actually perform TPC is about 1 h, it is seen that the equilibration time substantially increases the total time of the measurement. It is desirable that this time be shortened. It is especially desirable that the equilibration can be done simultaneously with sample treatment, thereby decreasing the time to nearly zero. However, prior art devices do not have the appropriate fluid paths to permit this.

The response of a TCD is inversely proportional to the volume flow rate through it, so accurate control of flow is important. Prior art devices use a flow controller which is upstream of the sample chamber and do not provide means to measure the true flow through the detector. Although the use of a mass flow controller is common, it is not realized that the increase in temperature of the reactor and adsorption or desorption processes within the reactor will result in flow changes downstream of the reactor.

A design problem in TPC utilizing a TCD is the wide dynamic range of a TCD. In a well designed apparatus, signals of several $\mu V$ need to be measured, but a signal can be as high as about 1 V. Prior art apparatus do not provide adequate resolution and dynamic range. The Altamira AMI-1 uses a 12 bit analog to digital converter, which is a very common device for automated data collection. The converter has an adequate resolution of 5 $\mu V$, but the range is only 20 mV. If a signal exceeds this value the data is lost. It is therefore desirable to provide a wide dynamic range with good resolution.

Another major design problem in TPC, and especially when a TCD is used, is maintaining a stable baseline and rejection of noise. Baseline drift usually limits the sensitivity of a measurement. It is well known to those skilled in the art of processing low level signals, that 60 Hz noise is a major problem. It is commonplace to filter out 60 Hz noise, but filtering over a much wider time span not usually done since this can distort the true signal. It is also common after doing TPC to calibrate the response of the TCD by using a gas sampling valve to inject pulses of gas into the TCD. The peak width of these pulses is about 1 s, which also precludes heavy filtering. Therefore, it is unexpected that filtering could be done over a time span of several seconds without distorting the desired signal, thereby substantially reducing noise and increasing the accuracy of the TPC measurement.

A common form of TPC is temperature programmed reduction in which a dilute stream of hydrogen in argon is used. The practice is to limit the current of the TCD to the maximum value specified for pure argon, which is much lower than for pure hydrogen. Low concentrations of hydrogen are used because the sensitivity of the TCD drops rapidly at higher concentrations. Typical concentrations are 5 to 10% hydrogen, and concentrations from 2 to 20% have been reported. A disadvantage is that reductions of solids are often done at one atmosphere of hydrogen, so this TPC data is acquired at partial pressures of hydrogen about 10-fold less than used in a typical reduction. Adequate sensivity during TPC can be a problem, and is largely due to drift of the TCD during the process. It is therefore desirable but unexpected to be able to construct an apparatus for TPC utilizing a TCD which can be effective at unusually high concentrations of hydrogen. It would be especially surprising if this could be done with only slight loss of sensitivity.

The established method of TPC utilizing a TCD is here defined as the series mode. In this mode a flow of reaction gas enters the reference side of the TCD, then passes through the reactor, and then into the sample side of the TCD. The series mode guarantees equal flow in both sides of the TCD and has minimal components. The established use of the series mode makes the design of a TPC apparatus providing for simultaneous TPC of more than one sample unexpectedly complex. Simultaneous TPC can not be done in this mode. A parallel mode is required which splits the stream of reactant gas into two pans, each of which must be separately controlled. One flow passes through the reactor and the sample side of the TCD, and the other flow passes only through the reference side of the TCD.

No prior art TPC apparatus enables the simultaneous analyses of more than one solid. Using multiple apparatuses simultaneously is expensive, and using one apparatus sequentially is slow. A person skilled in the art of TPC and computer programming could combine the components of automated TPC apparatuses into a single apparatus, but the primary savings would only be from the use of a single computer. It is therefore desirable to achieve simultaneous TPC at reasonable cost. In practice, it is common to perfrom a series of TPC on different samples but using the same reaction gas. By clever recognition of this and the judicious choice and arrangement of components, it is an object of this invention to achieve simultaneous TPC at a cost only slightly higher than for single TPC.

It is therefore a further object of the present invention to provide an apparatus which can perform TPC as well as measure the reaction, adsorption, and desorption of a gas with a solid at low, ambient, and high pressures including the ability to accurately measure the amount of gas adsorbed on or desorbed from a solid utilizing the volumetric method. Other objects of the present invention are to greatly lower the equilibration time for TPC, improve noise rejection, provide means for simultaneous TPC, and provide controlled cooling of a solid sample in such a manner that measurements of temperature programmed adsorption can be performed.

The prior art devices previously described which only operate in the pressure regime at or below about 1 atm have no means of controlling or measuring high pressure gases and the introduction of high pressure gases could easily damage components of the apparatus and possibly cause the apparatus to explode.

Menon (Catalyst Deactivation, Marcel Dekker, Inc. 1988, b. 101) describes the use of a mass spectrometer as the detector for temperature programmed desorption done by the flowing gas technique. A mass spectrometer operates at pressures $<10^{-5}$ torr, so it is contained in its own evacuated chamber of large volume. It is necessary to reduce the presssure of the portion of the effluent gas which is analyzed. A common method is to pass some of the gas through a molecular leak so that a very small amount of gas is bled into the evacuated chamber containing the mass spectrometer probe. This pressure reduction leads to a very large degradation of the signal to noise ratio in the mass spectrometer. For this reason some companies, such as UTI of Milpitas, Calif manufacture an unconventional ion source, called a closed ion source, for the mass spectrometer which reduces but does not eliminate this problem.

Another method of performing temperature programmed desorption is to monitor the gas phase as the sample is evacuated after being exposed to an adsorbate. This method is here defined as temperature programmed desorption by direct evacuation. In particular, in this method a solid sample contained in an evacuable chamber is exposed to an adsorbate. The temperature of the sample is then raised at a known rate while the sample chamber is evacuated and an analyzer contained in an evacuated chamber continuously measures some parameter of the desorbed gas The standard practice is to place both the solid sample and a mass spectrometer probe within the same large evacuated chamber. This method has much higher sensitivity than the flowing gas technique. However, only samples of relatively low surface area can be used and the apparatus normally only operate at high vacuum. This conventional method of performing temperature programmed desorption differs substantially from the method of the present invention in which the mass spectrometer probe is place in a separate evacuated chamber and the reactor is in air and is isolatable from the evacuated chamber by means of a shutoff valve.

In 1976 Blakely et. al. (J. Vac. Sci. Technol. volume 13, number 5, 109) described an ultra high vacuum apparatus which was modified to enable monitoring chemical surface reactions on single crystals over a wide pressure range. The apparatus incorporates analysis methods used in surface science including low energy electron diffraction and mass spectrometry means which are contained in a large ultra high vacuum chamber. The vacuum chamber was modified to enable a removable cup to be placed over the sample and the cup has gas lines, essentially forming a reactor. The reactor is contained within the large chamber which is at high vacuum. It is alleged that reactions can be done at pressures up to 100 atm within the cup. This arrangement is very cumbersome and is very limited in application. This distinguishes from the present invention, wherein the reactor is exposed to air and is isolatable from vacuum by a shutoff valve.

This device differs in many other ways from the present invention. The apparatus of Blakely only enables reactions to be done on single crystals using samples having a total surface area of about $1 \times 10^{-4} m^2$, corresponding to a specific surface area of $<0.01\ m^2/g$. However, very few materials are single crystals, no practical catalyst uses single crystals, and all practical catalysts have much higher surface area. A typical value for a practical catalyst is 100 $m^2/g$, so that a typical sample size of 1 g has a surface area $10^6$-fold higher than capable of being used in the Blakely apparatus. This apparatus has no sample holder to contain a powdered or pelleted sample, whereas almost all catalysts are of this type. The present invention has no restriction on the specific surface area of a sample and the, sample chamber accommodates powdered and pelleted samples. No means is described for cooling a sample in the Blakely apparatus, so neither the surface area nor pore structure of a solid can be determined with this apparatus. The apparatus also has no dosing volume, so measurements can not be made of the amount of adsorption and desorption of a gas with the sample using the volumetric technique. Reactions can only be done in the circulating mode, whereas the present invention enables the more useful methods of the flow mode and batch mode as well as being operable in the circulating mode.

Accordingly, it is also an object of the present invention to provide a means of using a mass spectrometer to monitor the desorption of a gas from a solid of specific surface area from about 0.01 to 1500 $m^2/g$ in such a manner as to substantially increase the sensitivity of the measurement over the conventional value and achieve this improvement without the complication and expense of a closed ion source.

Thermogravimetric analysis (TGA) is another useful technique for measuring the interaction of a solid with a gas. A TGA apparatus primarily consists of a microbalance and sample holder contained in a controlled atmosphere enclosure. Sometimes the enclosure is evacuable. A furnace heats the sample holder, so the weight of a sample can be determined as a function of temperature. TGA apparatus are made by several companies, such as Cahn Instruments of Cerritos, Calif. None of the prior art TGA apparatuses can be used for measuring the interaction of a gas with a solid by the volumetric method, nor can be used for TPC, nor are suitable for measuring a chemical reaction of a gas catalyzed by the solid. In order to increase the speed of acquiring results and lower equipment cost, it Would be desirable to integrate other functionality into a TGA apparatus.

It is evident that a wide temperature range is encountered in the variety of measurements which are used to measure the reaction, adsorption, or desorption of gases with a solid. For example, measurements of the surface area and pore structure of solids are routinely done at $-196°$ C. Many chemical reactions and pretreatments of solids require high temperatures. For example, gamma alumina, which is an important catalyst support, undergoes substantial changes in its physical properties at temperatures near 1200° C.

With the aforementioned prior art, much time is lost by the relatively slow heating of furnaces to reaction temperature and the subsequent slow cooling of a furnace. The slow thermal response of a furnace is exacerbated if it must be capable of operation at very high temperatures. This is because safety considerations generally limit the temperature which the outer surface of a furnace can have, and this in turn requires additional insulation of a furnace. Larger furnaces in term have larger heal capacity which slows heating and cooling. For example, ATS of Butler, Penn., manufacturers a model 3110 tube furnace with a temperature rating of 1200° C. This furnace is alleged to heat and cool very fast. The minimum O.D. recommended for the furnace is 8". The heating rate of this furnace is about 40° C./min. Cooling is found to be quite slow below 100° C. Similar furnaces are available with temperature ratings up to 1650° C. A typical time for pretreating a catalyst or effecting a chemical reaction of a gas with a solid at a temperature of 1200° C. is <1 h. Therefore, the time spent heating and cooling substantially increases the total time of the process.

Therefore, it is an object of this invention to provide an apparatus which can measure the reaction, adsorption, or desorption of a gas with a solid over a very wide range of temperature, including temperatures up to 1650° C., and which can heat and cool a reactor extremely quickly. It is also an object of this invention to provide means for a furnace and insulated container containing a cryogenic fluid to be very rapidly removed and installed on an apparatus so the temperature of a sample can be changed over the range of from $-196$ to 1650° C. in only a few minutes.

Glass reactors are widely used for chemical reactions. Compared to reactors constructed of metal, glass has the advantages of being transparent, more chemically inert, and capable of withstanding higher temperatures. For example, stainless steel (SS) is the most common metal used to construct chemical reactors. The temperature limit for SS for such an application is approximately 500° C., and in some cases deleterious reactions with chemical feedstocks occur at much lower temperature. Reactors made of fused quartz are usable to above 1200° C. Ceramics, such as fused alumina, can be used to construct reactors of substantially higher temperature rating.

The major disadvantages of glass and ceramics are they can not withstand high pressures and are fragile. When a glass reactor is attached to a metal reaction system, there are two main places in which breakage occurs. The first is at the ends of the reactor where fittings couple the reactor to the rest of the apparatus. Breakage occurs due to the glass being crushed by the compressive forces of the fitting. In many cases the reactor has a U shape, with a gaseous or liquid fluid entering one arm and exiting from the other. In this case, a second weak spot is the bottom of the U. Breakage occurs here due to torque transmitted to the reactor when the fittings are tightened. Although various manufacturers claim their fittings to be free of torque, when used with a glass U shaped reactor experience shows that breakage is common.

One method to prevent the first type of breakage is to use a glass to metal seal. Such seals are commercially available, are leak tight, and provide a metal termination for a reactor. In some cases a soft elastomer, such as VITON rubber, is used to make the seal so only modest compressive forces are required. While this reduces breakage of the first type, it does not eliminate it and elastomers are less chemically inert and adsorb and desorb gases more than metal or glass. This lowers the accuracy of measurements of the adsorption or desorption of a gas with a solid made by the volumetric technique.

Breakage of the second type can be reduced by constructing a glass bridge between the two arms of the reactor. However, excessive torque will now cause the reactor to break at the position of the bridge. Micromeritics avoids this problem by using a reactor which has only a single point of attachment to the rest of the system, thereby eliminating the U shape. This is achieved by using concentric tubing to provide means of both entrance and exit for gas. However, this design suffers from the need to have elastomeric O-ring seals within the reactor with the aforementioned undesirable features and in addition the design results in a much lower gas conductance than a design which does not use concentric tubes and this will substantially slow evacuation of the reactor.

It is therefore an object of this invention to provide a glass reactor which is free of elastomers, has a high conductance for evacuation, can be attached to an apparatus in a leak free manner, and which is resistant to breakage.

It is seen that devices for the control and measurement of the flow of gases at high and low pressures are widely used in apparatus which measure the reaction, adsorption, and desorption gases with solids. Further, control and measurement of the gas environment is crucial to the operation of such apparatus and frequently limits the operating range of such apparatus. In describing the nature of existing devices, it is useful to divide pressure into three regimes: the low pressure regime consists of pressures below 1 atm, the high pressure regime consists of pressures above 30 psia, and the ambient pressure regime refers to the range bounded by 1 atm and 30 psia.

To achieve pressures much below 1 atm requires the use of a vacuum pump. A rotary pump may be used to achieve a pressure of about $10^{-3}$ torr, but lower pressures require both a rotary pump and a second pump of the high vacuum type, such as a diffusion pump or turbomolecular pump. Such pumps can achieve an ultimate vacuum of about $1\times10^{-9}$ torr, but can not operate above about 0.3 torr. Further, exposure of such pumps to pressures above about 0.3 torr can damage the pump. For this reason, the attainment of high vacuum requires a rotary vacuum pump, a high vacuum pump, multiple valves, evacuation paths, and a pressure gauge operable near 0.3 torr so that the pressure can be reduced below about 0.3 torr before the high vacuum pump is used to evacuate the chamber.

The measurement of pressure in the low pressure regime is also a specialized field, with various types of gauges being needed to cover the range from $10^{-9}$ torr to 1 atm. None of the gauges useful for measuring very low pressures can operate near 1 atm, and many of them will be damaged by exposure to a pressure above $10^{-2}$ torr. Gauges useful at very low pressures almost invariably operate on an ionization principle and are relatively inaccurate. A separate gauge, usually a thermocouple or Pirani gauge, is necessary to measure pressure in the range of about 0.001 to 10 torr.

The design of a vacuum system requires great attention to the materials used with respect to such criteria as their mechanical integrity under vacuum, minimization of the adsorption of gases onto the walls of the system, outgassing of components, diffusion of gases through walls, extreme leak tightness of seals, inner diameter (I.D.) of tubing, and pumping speed. Speed of evacuation is an especially important and difficult design parameter.

At pressures below about 0.1 torr the mass transport of a gas occurs by molecular flow in most containers. The ability of a tube to transport gas is often measured by its conductance. In the regime of molecular flow, the conductance, C, of a tube is independent of the pressure and is approximately given by $$C=C_m=12.2d^3/l \; L/s$$

where d is the diameter and l is the length of the tube in cm. A tube which is 30 cm long will have a conductance of 87 L/s if its I.D. is 6 cm, and will have a conductance of $7\times10^{-6}$ L/s if its I.D. is 0.025 cm. At a pressure of $1\times10^{-6}$ torr, the former conductance corresponds to a rate of mass transport of a gas with a specific gravity of 1 (such as $N_2$) of $1\times10^{-4}$ mL STP/s, an extremely low value.

The critical affect of the I.D. of tubing on the performance of vacuum systems can also be demonstrated by the following example. The time to evacuate a volume of size V from an initial pressure of $P_i$ to a final pressure of Pf if the volume is connected to a vacuum pump of pumping speed S by tubing of conductance C is $$t=(V/S_{eff})ln(P_i/P_f)$$

where the effective pumping speed, $S_{eff}$, is given by $$1/S_{eff} = 1/S + 1/C.$$

A pumping speed of about 100 L/s is typical for a high vacuum pump. Consider a volume of 0.1 L which is to have its pressure reduced from $7.6 \times 10^{-2}$ to $7.6 \times 10^{-4}$ torr (a factor of 100) and is connected to a vacuum pump of speed 100 L/s by a 30 cm length of tubing with an I.D. of either 6 cm or 0.05 cm. Tubing with an I.D. of 6 cm yields an evacuation time of 0.01 s, and tubing with an I.D. of 0.05 cm yields an evacuation time of $9 \times 10^3$ s.

In order to achieve reasonable rates of evacuation, it is therefore common for the I.D. of tubing in an apparatus capable of achieving a good vacuum to be at least several centimeters. Tubing used in vacuum systems is generally of wide bore and thin wall.

The proper selection of valves is also critical in an apparatus which functions at low pressure. In order to obtain pressures $<10^{-7}$ torr it is generally necessary to use packless valves which are also free of lubricant and are tested to be very leak tight. The orifice of the valves must be of substantial size to avoid restricting the pumping speed of a system. Packless valves are more expensive and available in much less variety than packed valves.

The criteria for the design of apparatus which transport gas at only modest vacuum and at high pressure are quite different. At pressures above about 1 torr the mass transport of a gas often occurs by laminar flow. In this pressure regime, the conductance of a tube depends on pressure and is approximately given by $$C = C_l = 183 d^4 P/l \; L/s$$

where d is the diameter and l is the length of the tube in centimeters and P is the average pressure in the tube in torr. A tube which is 30 cm long and has an average P of 760 torr will have a conductance of $6 \times 10^6$ L/s if its I.D. is 6 cm, and will have a conductance of $2 \times 10^{-3}$ L/s if its I.D. is 0.025 cm. A tube which is 30 cm long, has an I.D. of 0.025 cm, and has an inlet pressure of 3 atm and an outlet pressure of 1 atm is found to transport $N_2$ gas at a rate of 410 mL STP/s. Typical flow rates of gases in laboratory scale gas and reaction systems operating at $\geq 1$ atm are 0.1 to 30 mL STP/s. Therefore, mass transport is not a problem in this pressure regime.

An additional illustration is provided by the previous example of evacuation time except in this instance the pressure is to be reduced from 760 to 7.6 torr (a factor of 100) and the speed of the vacuum pump is 1 L/s, a value typical of rotary pumps. Tubing with an I.D. of 6 cm yields an evacuation time of 0.5 s, and tubing with an I.D. of 0.05 cm yields an evacuation time of 33 s. Further, the reduction of pressure from $>1$ atm to 1 atm is rapidly accomplished by venting a chamber and without the use of a vacuum pump.

It is therefore seen that the mass transport of gases in the high pressure regime occurs by a different process and at much higher rates than in the low pressure regime. Further, the ability to transport a given amount of gas is rarely a design concern in the high pressure regime and tubing of relatively small I.D. can be used. Tubing used in pressurized systems is generally of small bore and thick wall.

The maintenance and control of high pressure in a chamber through which gas flows also requires some type of regulating device to isolate the high pressure zone from atmospheric pressure. This is commonly done with a device such as a back pressure regulator. It has also been noted that the type of gauge used for measuring high pressure differs from that operable at very low pressure.

Valve selection for pressurized systems is normally straightforward. High pressure valves usually are not rigorously tested for leak tightness under vacuum and contain lubricants. Orifice size is not a concern for the flow rates used in laboratory scale apparatus. For example, a valve designed to attach to tubing of outer diameter 0.25" will pass $1.5 \times 10^4$ mL STP/s of air with a pressure drop of only 10 psi across the valve. As the pressure rating of an apparatus increases, the selection of valves and components suitable for high vacuum performance rapidly decreases and the price and complexity of the apparatus increases. For these reasons, there are breaks in the design of such an apparatus at pressures of about 200, 1000, and 3500 psia. In particular, at pressures above 3500 psi only packed valves are readily available.

The introduction of more than one pressurized gas into a common volume can cause back flow of one gas into the supply line of another gas. To prevent this hazardous situation, apparatus operating at high pressure contain check valves. This hazardous situation is not of concern in machines operating below 1 atm and a check valve would prevent the evacuation of any volume on the upstream side of the check valve.

It is also common practice to include filters in the flow lines of pressurized apparatus. The filters trap particulate matter which can damage valves and other components. Such particulates can be transported by the flow of gases and liquids in a pressurized machine, but are not readily transported in a vacuum. Conventional sintered disc metal filters, which have a surface area of about 0.04 sq. in. when placed inside of $\frac{1}{4}$" O.D. tubing, do not significantly impede the flow of gas in pressured devices. Filters are not normally used in tubing to be evacuated and will normally greatly reduce the speed of evacuation. More specialized filters of large surface area, typically $>0.2$ sq. in., are also available. Such a filter is usually contained in a holder having a volume of about 13 mL. The use of two such filters to protect against particulate matter in a reactor would degrade the accuracy of a measurement by the volumetric technique of the amount of gas adsorbed or desorbed with a solid by a factor of about two. It is seen that filters of exotic design are required in order not to seriously degrade both the pumping speed and the sensitivity of an apparatus used for volumetric adsorption measurements.

It is sometimes necessary to measure the amount of gas adsorbed on or desorbed from a solid sample of large particle size, such as a catalyst pellet. This requires a large I.D. of the tubing in the reactor. As previously described, extra volume can decrease the accuracy of such measurements.

When running reactions of a gas over a catalyst in a metal reactor, sometimes it is important to avoid side reactions with the walls of the reactor. This is especially a problem with TPC, since even slight side reactions can invalidate the results. There are a number of ways to minimize the problem. A glass liner is one approach, but it is difficult to avoid gas flow in the annular space between the liner and the wall of the reactor. This is especially difficult if the reactor is U shaped. Supporting a solid catalyst and cleaning a tubular reactor can also be problems.

The design of a multifunctional apparatus causes many complex problems in design which do not appear in more limited apparatus. One such problem is the use of a gas sampling valve (GSV). When characterizing a solid it is sometimes desired to pass pulses of a gas over a sample contained in a reactor. This requires that the GSV be plumbed so its pulse output is upstream of the reactor. However, in controlling chemical reactions it is common to have a GSV downstream of the reactor so the GSV can direct pulses of the reactor effluent to an analyzer. While two GSV's can accomplish these needs, GSV's are expensive and require many gas lines to function. It is desirable to achieve both goals in a simpler and less expensive manner. It is an object of the present invention to accomplish this by clever design.

The combination of multifunctionality and multiple reactors compounds design problems. In a single reactor apparatus, if the effluent can be directed to one of two devices then it is straightforward to use a selector valve. However, if a multiplicity of reactor effluents can be directed to a multiplicity of devices, then the use of many selector or switching valves to accomplish this is both expensive and confusing to the user. It is an object of the present invention to provide a simple and inexpensive solution to this problem Commercial apparatus for measuring chemical reactions or the adsorption or desorption of a gas with a solid am normally contained in a suitable enclosure. If an apparatus is to be highly multifunctional, then it is likely that occassional changes in the fluid paths will be necessary. In addition, it is desirable to have easy access to the interior components for maintenance and troubleshooting. An enclosure makes such access difficult. A common practice when dealing with apparatus handling gas flows is to have various inlet and outlet valves mounted on the wall of the enclosure. However, this requires that the fittings be disconnected if it is necessary to remove the wall to get access to the interior. Especially if the apparatus is to operate at high vacuum or high pressure, it is desirable to minimize the number of fittings which must be manipulated. This presents a challenging design problem.

It is therefore also an object of this invention to provide an apparatus which operates at high and low pressures and which has unusually facile means of being modified and maintained.

It is seen that pressures below 0.001 torr are necessary for important and common methods of characterization of surfaces which involve measuring the adsorption and desorption of a gas with a solid. However, almost all reactions done for the purpose of obtaining a product or evaluating the reactivity of a solid are done at pressures 24 1 atm. It has been also shown that the physical laws governing the flow of gases, the type of equipment used, and design considerations are very different and often conflicting for the two pressure regimes.

Consequently,, a single apparatus that can accurately measure the reaction, adsorption, and desorption of a gas with a solid at low, ambient, and high pressures is not present in the examples of prior art discussed above.

SUMMARY OF THE INVENTION

The object of 1the invention is to provide an apparatus and method for unusually accurate and rapid measurement of the amount of gas adsorbed on or desorbed from a solid sample of surface, area from about 0.01 to 1500 m$^2$/g and to provide the apparatus with means for controlling and measuring the reaction, adsorption, and desorption of a gas with the sample over a wide range of flow, temperature, and pressure including pressures well below 1 atm and well above 1 atm. It is an object of this invention to provide an apparatus that can achieve pressures from $10^{-9}$ torr to 10,00 psia and flow rates from $8 \times 10^{-4}$ to $1.6 \times 10^3$ mL STP/s and temperatures from $-196$ to $1650°$ C. It is a further object of this invention to achieve simultaneous control of pressure, flow, and temperature over these ranges. It is still a further object of this invention to provide means of unusually rapidly changing the pressure and temperature.

These and other objects of the invention are achieved in part by having an unusually small volume for that pad of the apparatus for which the accuracy of adsorption or desorption measurements performed by the volumetric method increases with decreasing volume, the apparatus being highly leak tight, the apparatus being free of components in fluid communication with the reactor which significantly adsorb gas or outgas, providing improved glass and SS reactors, the apparatus having both a high pressure transducer and a separate and very accurate low pressure transducer, the apparatus having novel configuration of valves and other components to enable very high and very low pressures to be rapidly and safely achieved, the apparatus providing means to very rapidly heat and cool a sample, providing means for the effluent from a reactor to be analyzed by a variety of devices which provide information on the composition of the effluent and hence also provide information on the reactions which occur in the reactor and the nature of the solid sample, providing means for simultaneous reactions on different samples, providing improved methods of obtaining chemisorption results, providing improved noise rejection during TPC, providing means to perform many processes on the same apparatus, and providing means for convenient access to the interior of the apparatus so as to increase it range of application.

The apparatus is useful for many types of characterization of solids which require measuring the amount of gas which is adsorbed on or desorbed from a solid. It is especially useful for accurate measurements of the amount of gas adsorbed on or desorbed from a solid. The apparatus is also useful for measuring the reaction of a gas, including gasified liquids and solids, with a solid, and especially a catalyst. The reactor can contain liquids or solids, and especially solid catalysts. Measurements can be made of many kinetic parameters of chemical reactions.

An object of tits invention is to provide an improvement over prior art apparatus which perform these measurements. The improvement comprises the means to cover the low, ambient, and high pressure regimes in a single apparatus whereas prior art requires a plurality of apparatuses. An object of this invention is to provide means for these measurements to be made more quickly, at lower cost, and with less contamination than is achievable using multiple apparatuses. It is an object of this invention to provide an apparatus which in some instances enables measurements to made with higher sensitivity and accuracy than by the aforementioned examples of prior art. It is an object of this invention to provide an apparatus with means to control temperature over a wider range than practiced by the aforementioned examples of prior art.

The nature of the invention can be most easily understood by reference to the example of solid catalysts. Such materials are routinely characterized by apparatus which measure the adsorption of gases at pressures substantially less than 1 atm, but the reactivity of catalysts is routinely measured at pressures $\geqq 1$ atm which requires a different apparatus. Each of these techniques can be performed on a preferred embodiment of this invention.

The invention is not limited in its application to the details and construction and arrangement of parts illustrated in the company drawings since the invention is capable of other embodiments that are being practiced or carried out in various ways. Also, the phraseology and terminology employed herein are for the purpose of description and not of limitation.

BEST AND VARIOUS MODES FOR CARRYING OUT INVENTION

The present Invention is inherently modular in nature and therefore there is a wide range of specifications which can be designed into it. Correspondingly, there is great lattitude in the choice of components to be used in the construction of the apparatus. Such flexibility in specification and design is in itself unexpected and is not possible with prior art machines. This flexibility is illustrated in the embodiments shown in FIG. 1 to 7.

The following is a partial ist of the components shown on the diagrams and their abbreviated representations.

Figure 1:
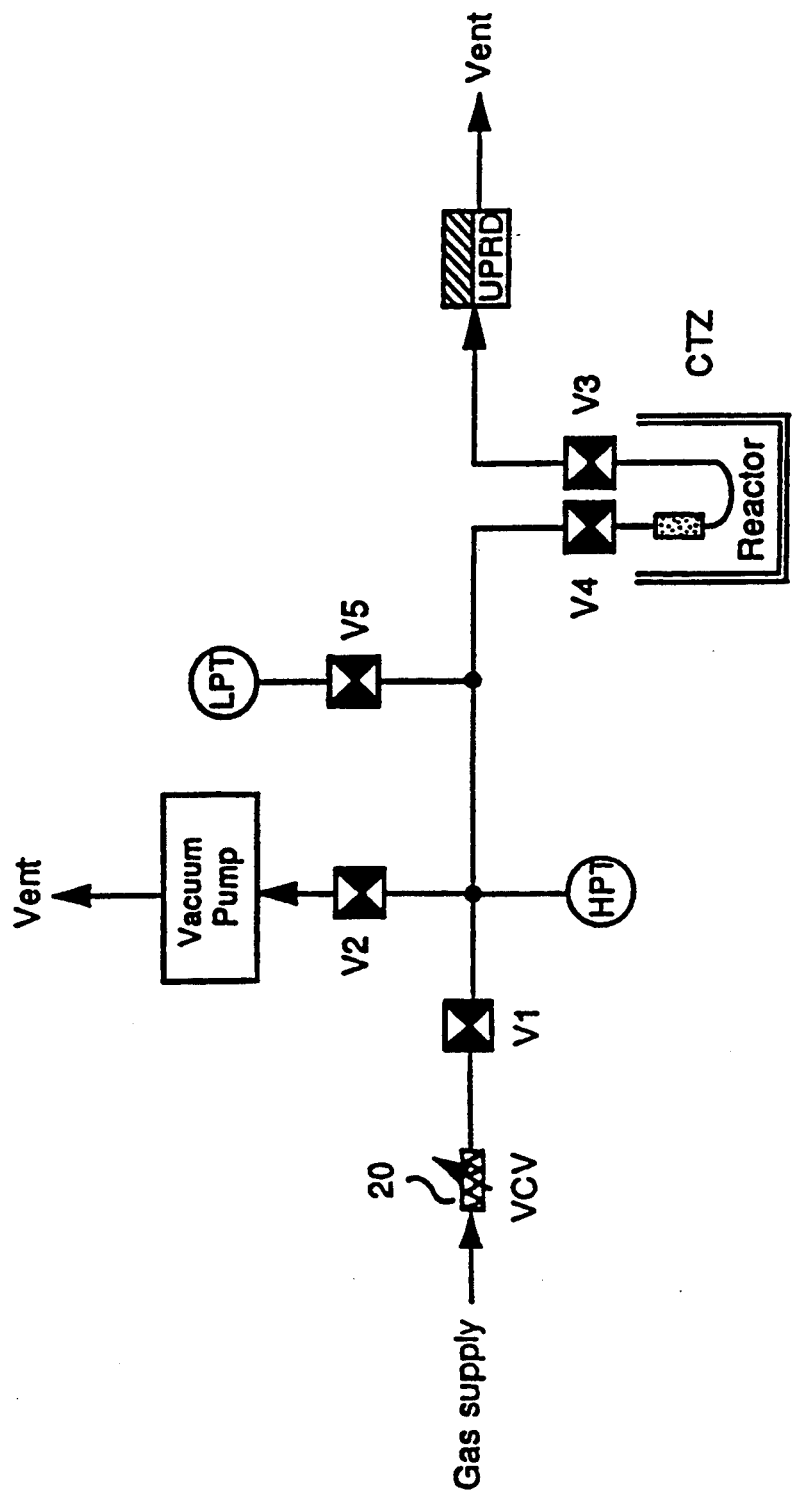
FIG. 1 is a diagrammatic representation of an alternative embodiment of this invention.

In FIG. 1 there is a variable conductance valve, 20, designated on the drawing as VCV.

Figure 2:
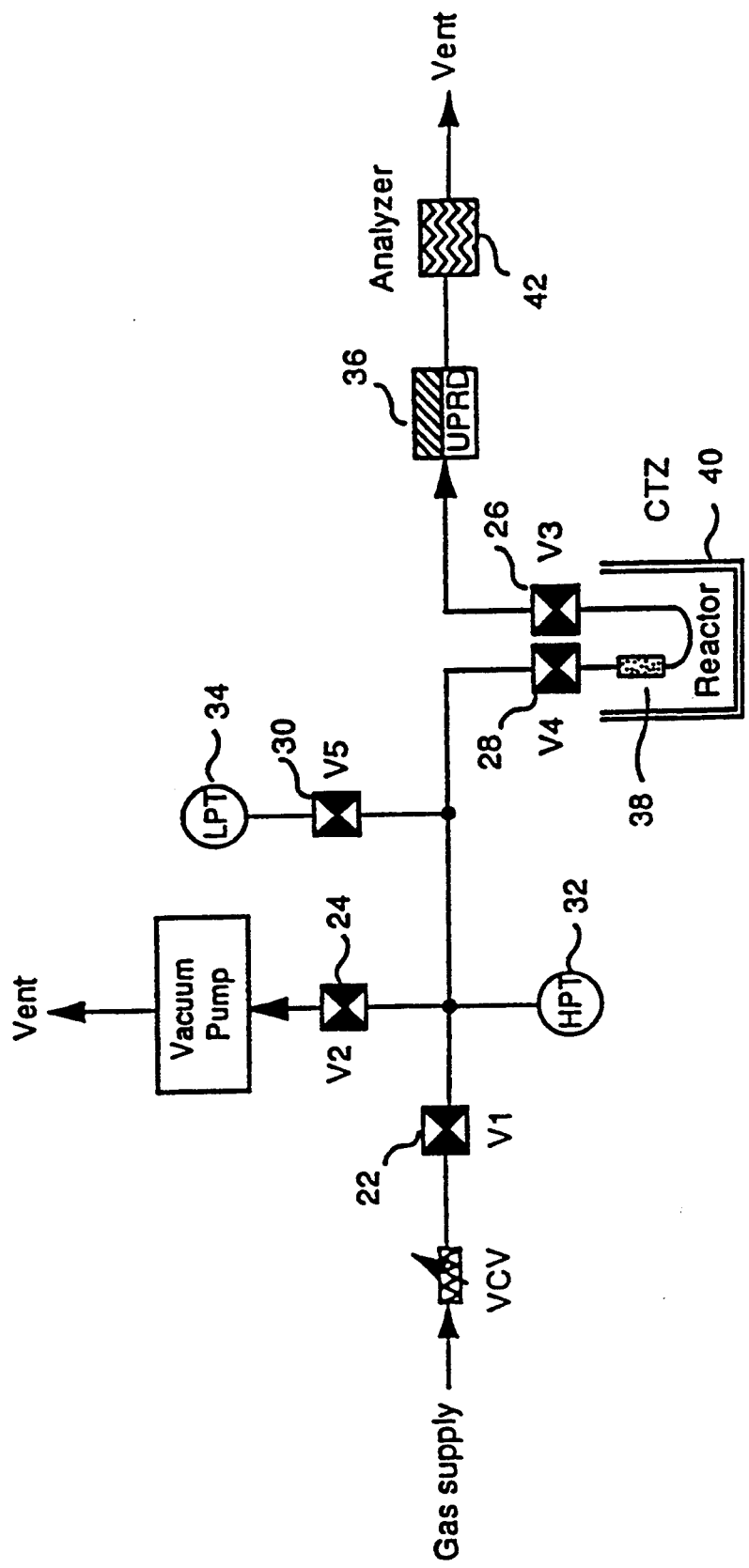
FIG. 2 is a diagrammatic representation of a preferred embodiment of this invention.

In FIG. 2 there is a shutoff valve, 22, is designated V1.

A shutoff valve, 24, is designated V2.

A shutoff valve, 26, is designated V3.
A shutoff valve, 28, is designated V4.
A shutoff valve, 30, is designated V5.
A high pressure transducer, 32, is designated HPT.
A low pressure transducer, 34, is designated LPT.
An upstream pressure regulating device, 36, is designated UPRD. An UPRD controls the pressure of gas upstream from it and allows the gas to flow through it, usually venting at atmospheric pressure.
A reactor, 38, is designated Reactor. A reactor is a chamber to hold a solid sample.
A controlled temperature zone, 40, is designated CTZ.
A gas analyzer, 42, designated on the drawing as Analyzer. An Analyzer is a means of analyzing least one parameter of a gas.

Figure 3:
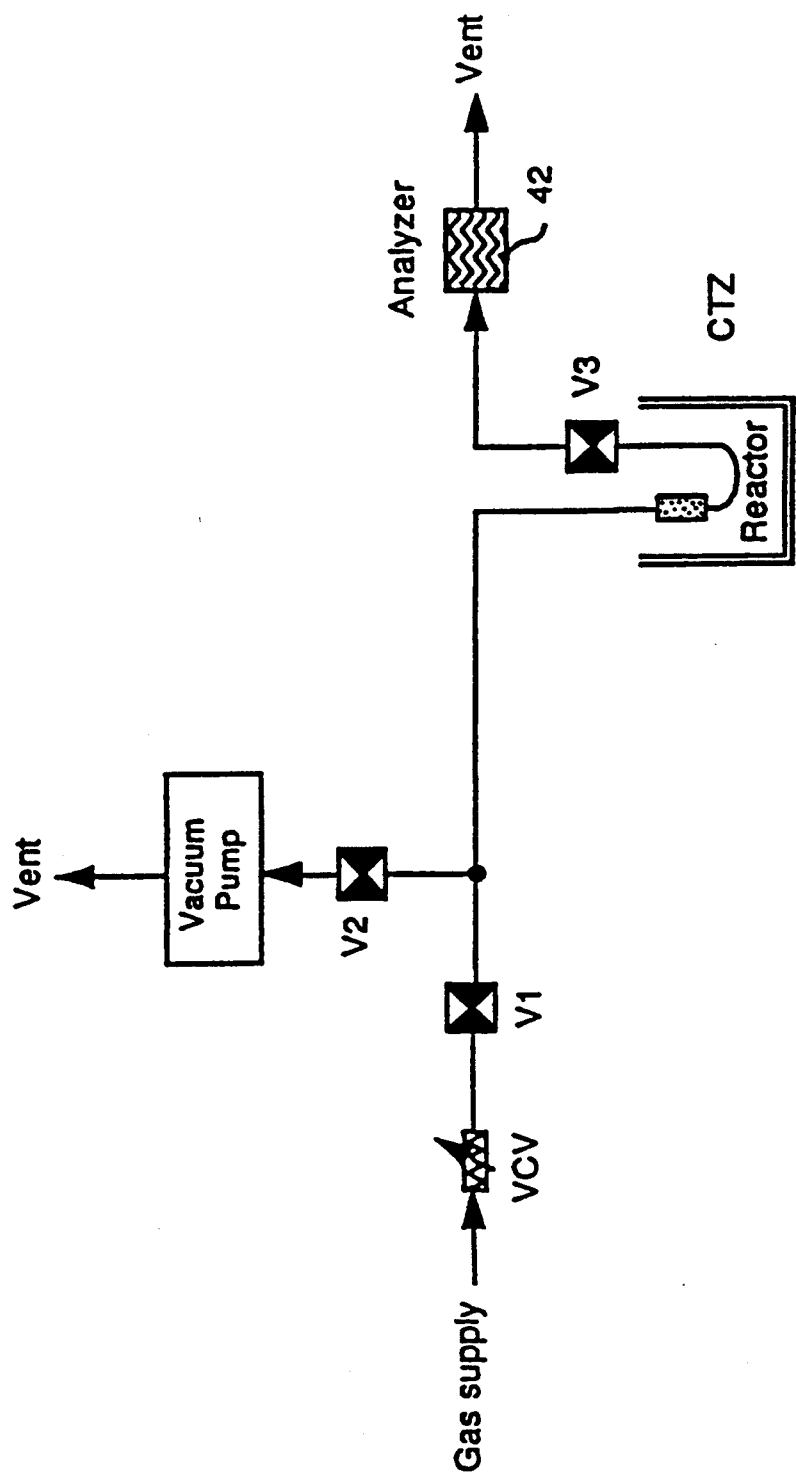
FIG. 3 is a diagrammatic representation of an alternative embodiment of this invention.

In FIG. 3 there is a gas analyzer, 42, designated on the drawing as Analyzer.

Figure 4:
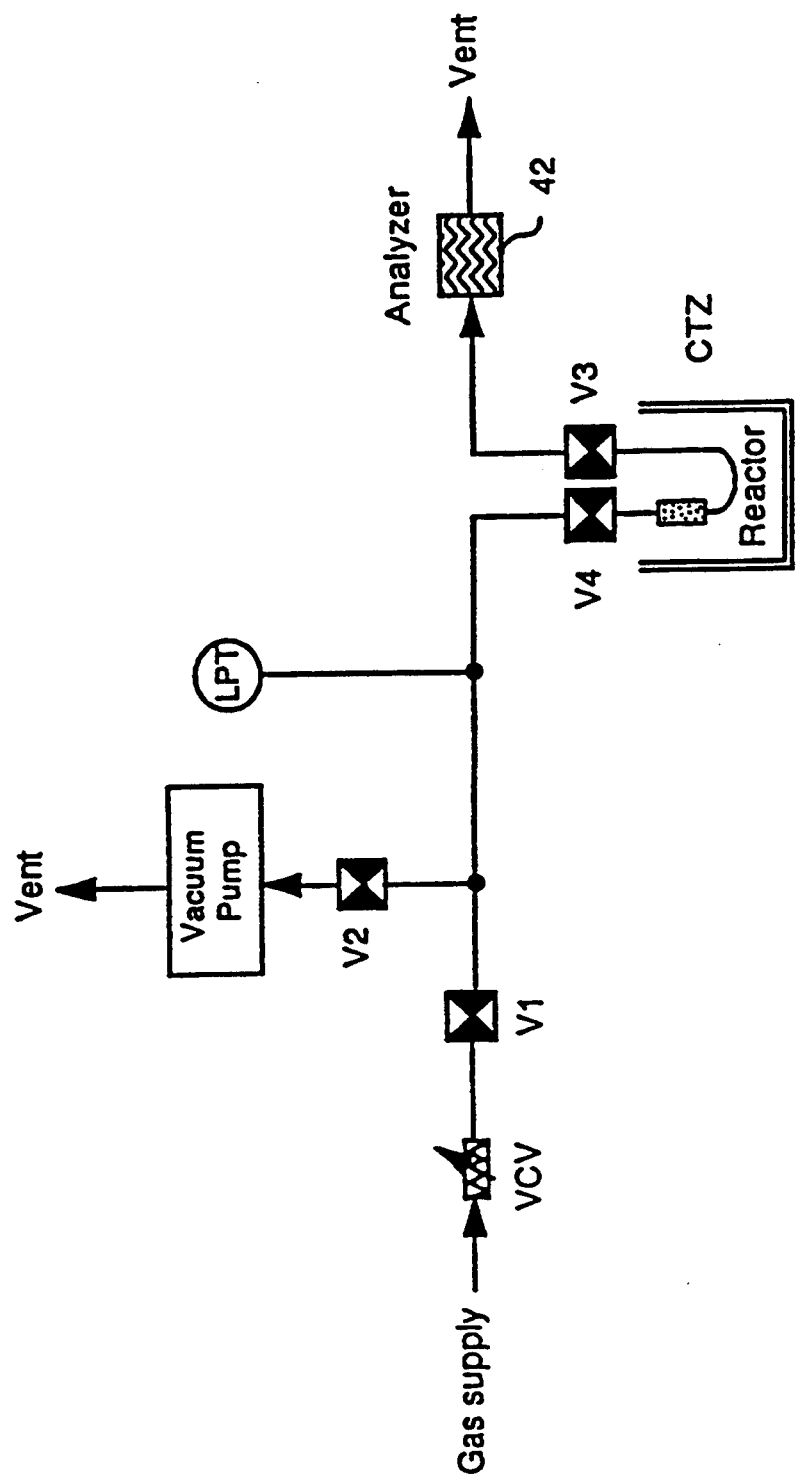
FIG. 4 is a diagrammatic representation of an alternative embodiment of this invention.

In FIG. 4 there is a gas analyzer, 42, designated on the drawing as Analyzer.

Figure 5:
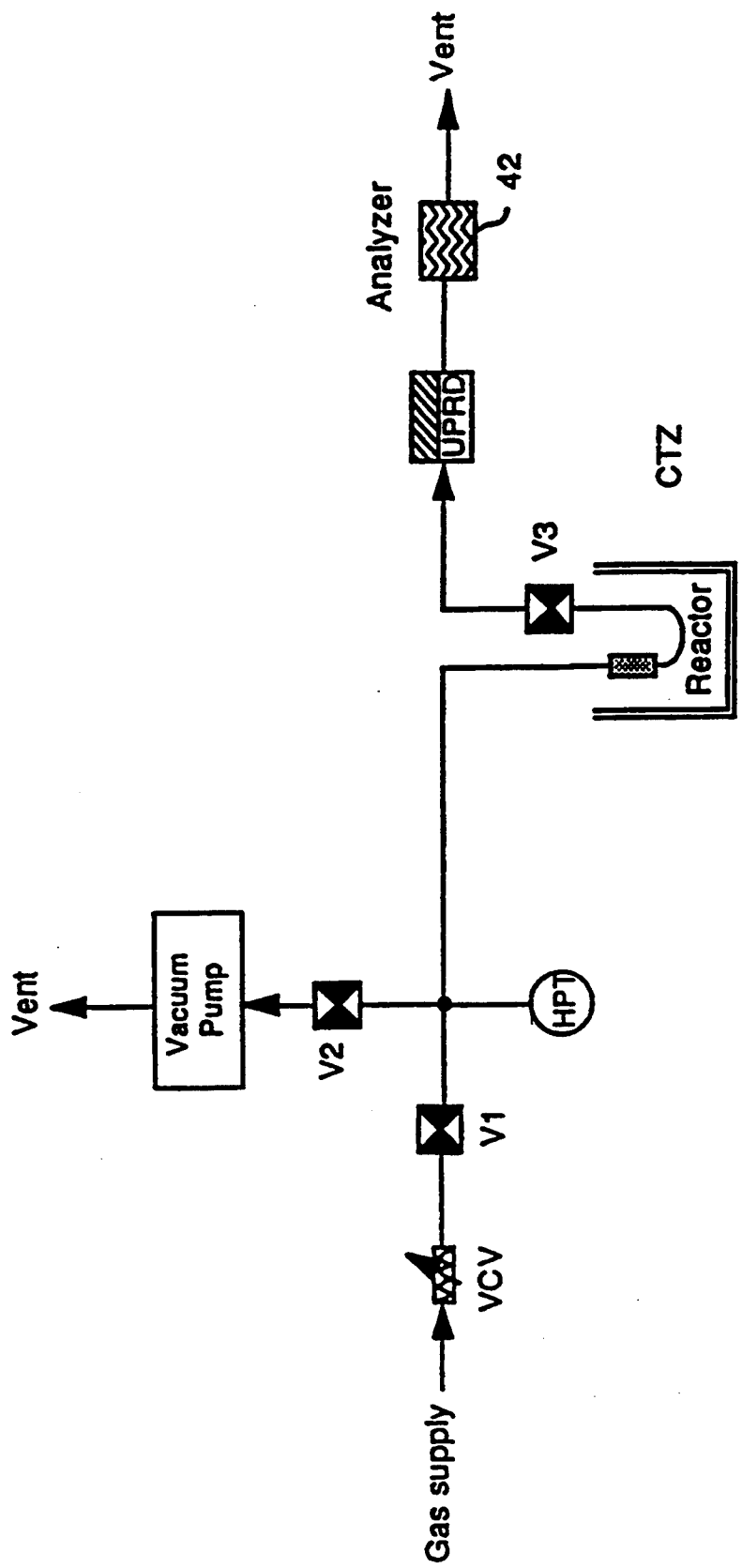
FIG. 5 is a diagrammatic representation of an alternative embodiment of this invention.

In FIG. 5 there is a gas analyzer, 42, designated on the drawing as Analyzer.

Figure 6:
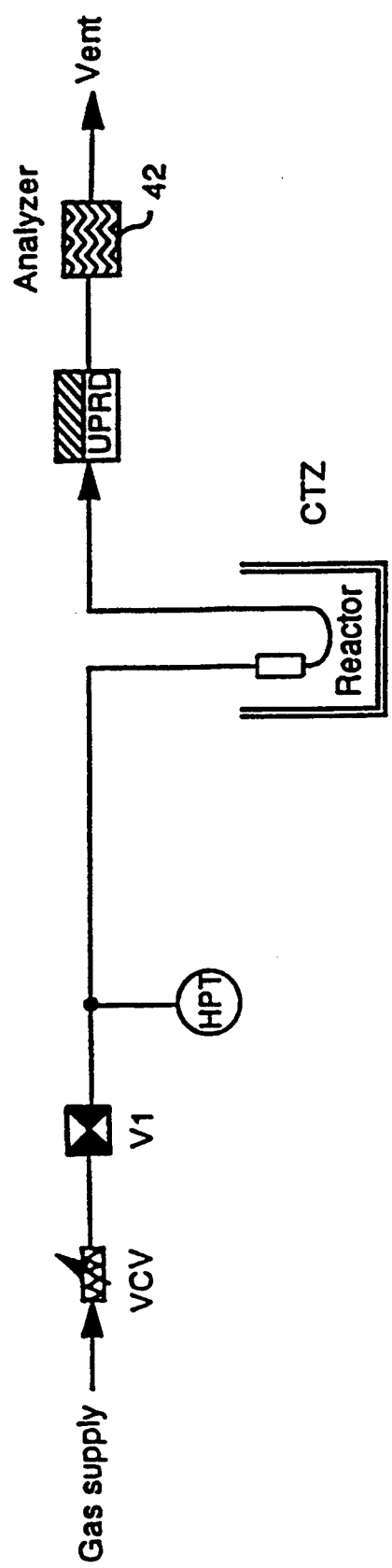
FIG. 6 is a diagrammatic representation of an alternative embodiment of this invention.

In FIG. 6 there is a gas analyzer, 42, designated on the drawing as Analyzer.

Figure 7:
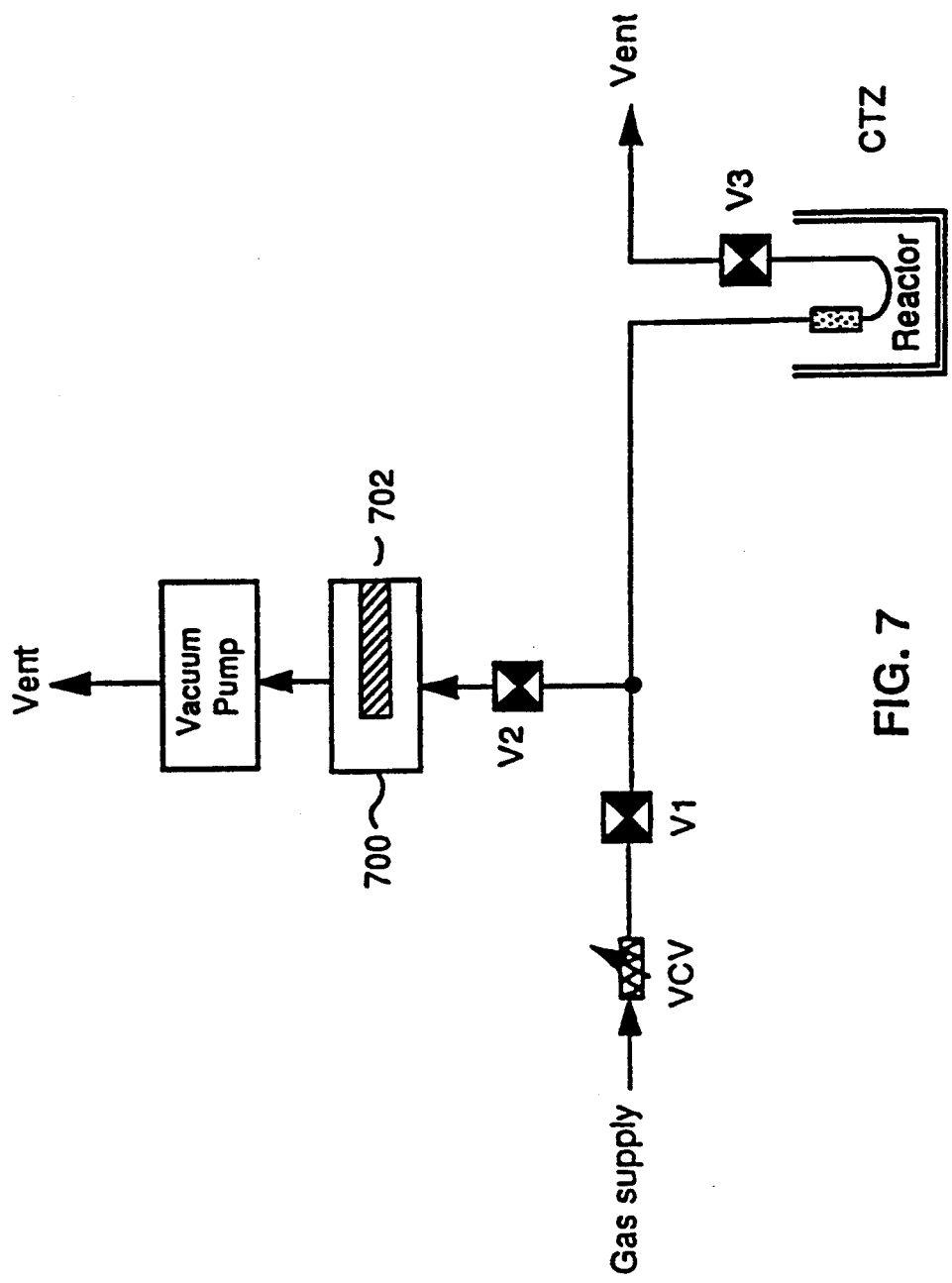
FIG. 7 is a diagrammatic representation of an alternative embodiment of this invention.

In FIG. 7 there is an evacuable chamber, 700.
A mass spectrometer probe, 702.

Figure 8:
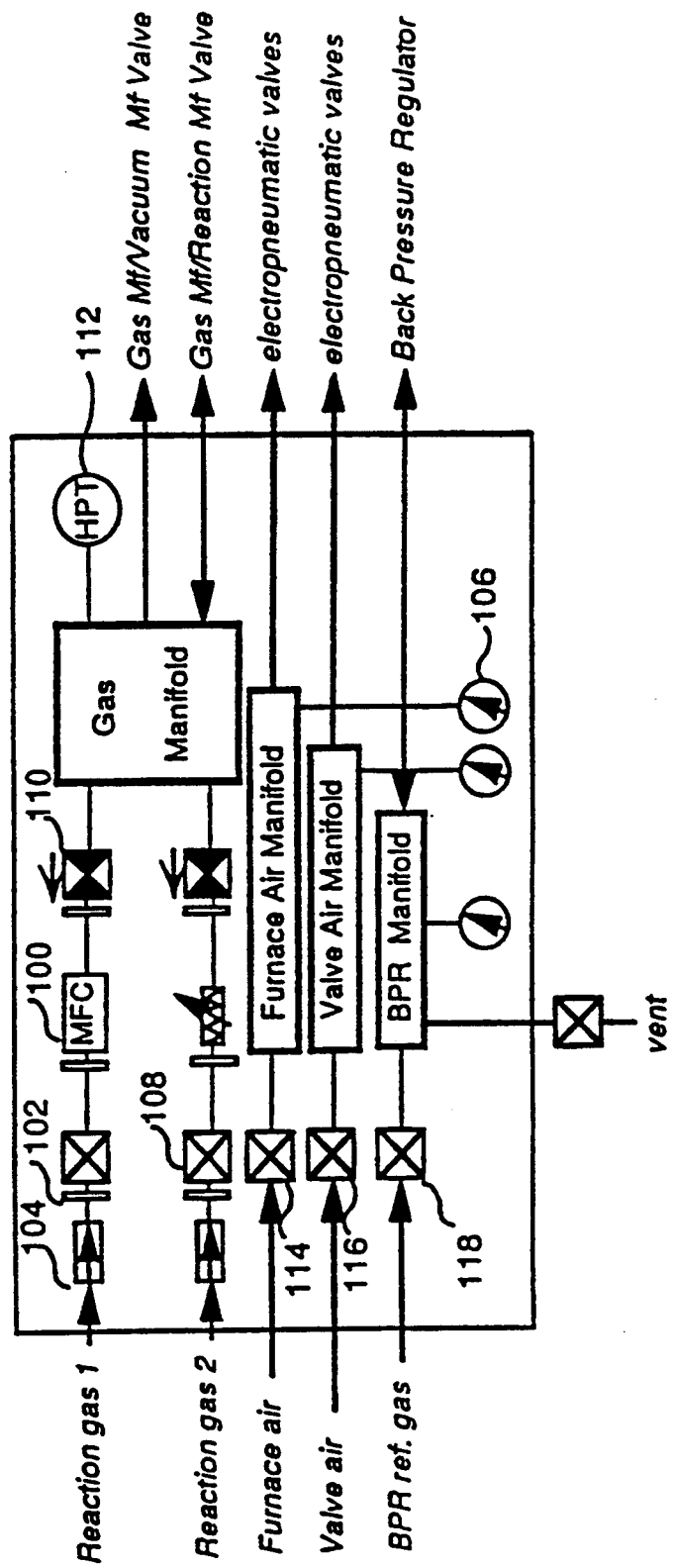
FIG. 8 is a diagrammatic representation of a portion of a preferred embodiment.

In FIG. 8 there is a mass flow controller, 100, designated on the drawing as MFC. A mass flow controller electronically controlls the mass flow rate of a gas.

A filter, 102.
A check valve, 104.
A pressure gauge, 106.
A shutoff valve, 108.
A shutoff valve plumbed in a direction opposite to that normally done, 110.
A high pressure transducer, 112.
A shutoff valve, 114.
A shutoff valve, 116.
A shutoff valve, 118.

Figure 9:
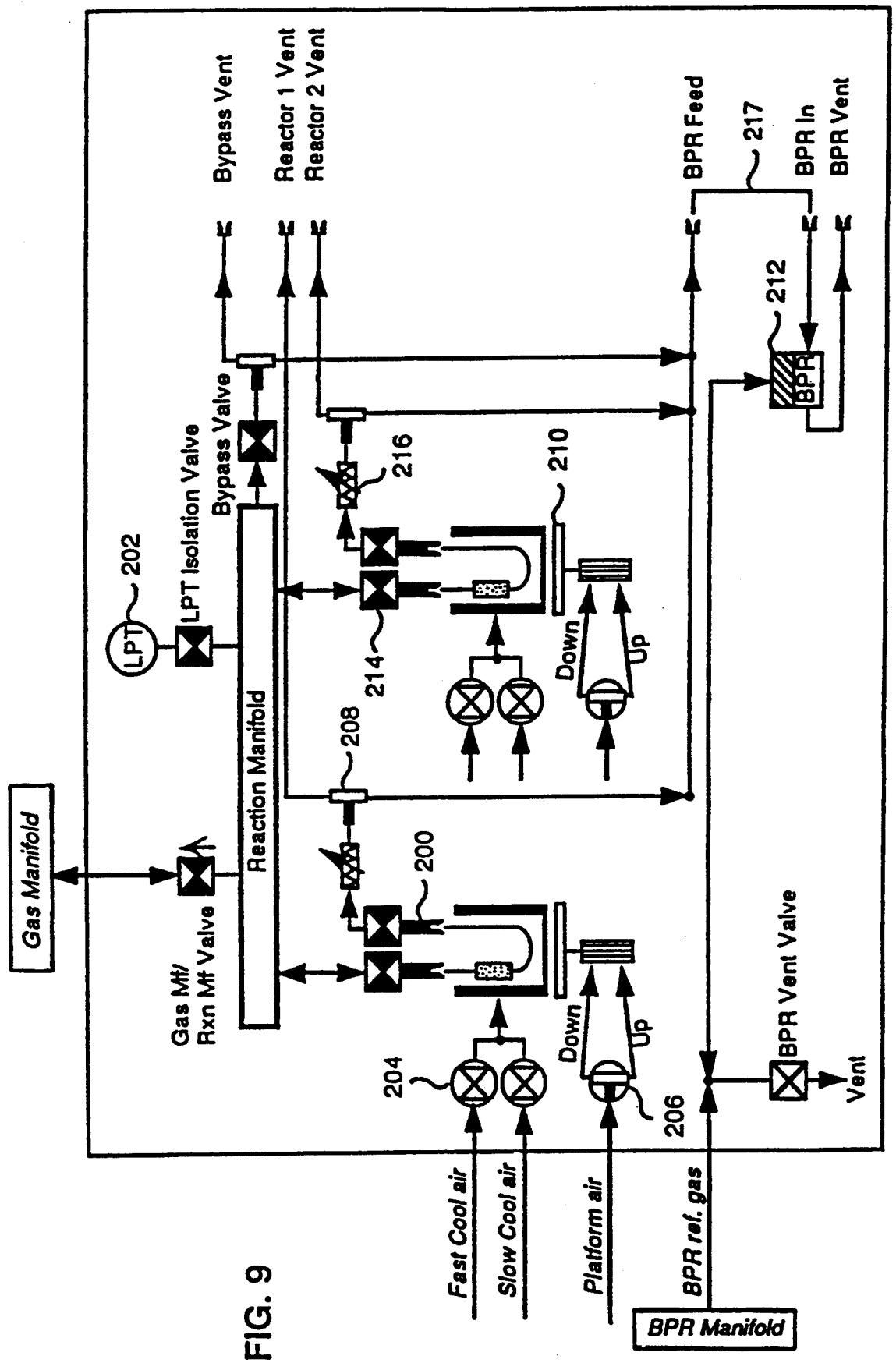
FIG. 9 is a diagrammatic representation of a portion of a preferred embodiment.

In FIG. 9 there is a reactor harness, 200.
A low pressure transducer, 202.
A remotely actuated valve, 204.
A remotely actuated selector valve, 206.
A selector valve, 208.
A pneumatic platform, 210.
A back pressure regulator, 212, is designated BPR.
A shutoff valve, 214.
A metering valve, 216.
A shunt, 217. A shunt is a removable piece of tubing for gas flow.

Figure 10:
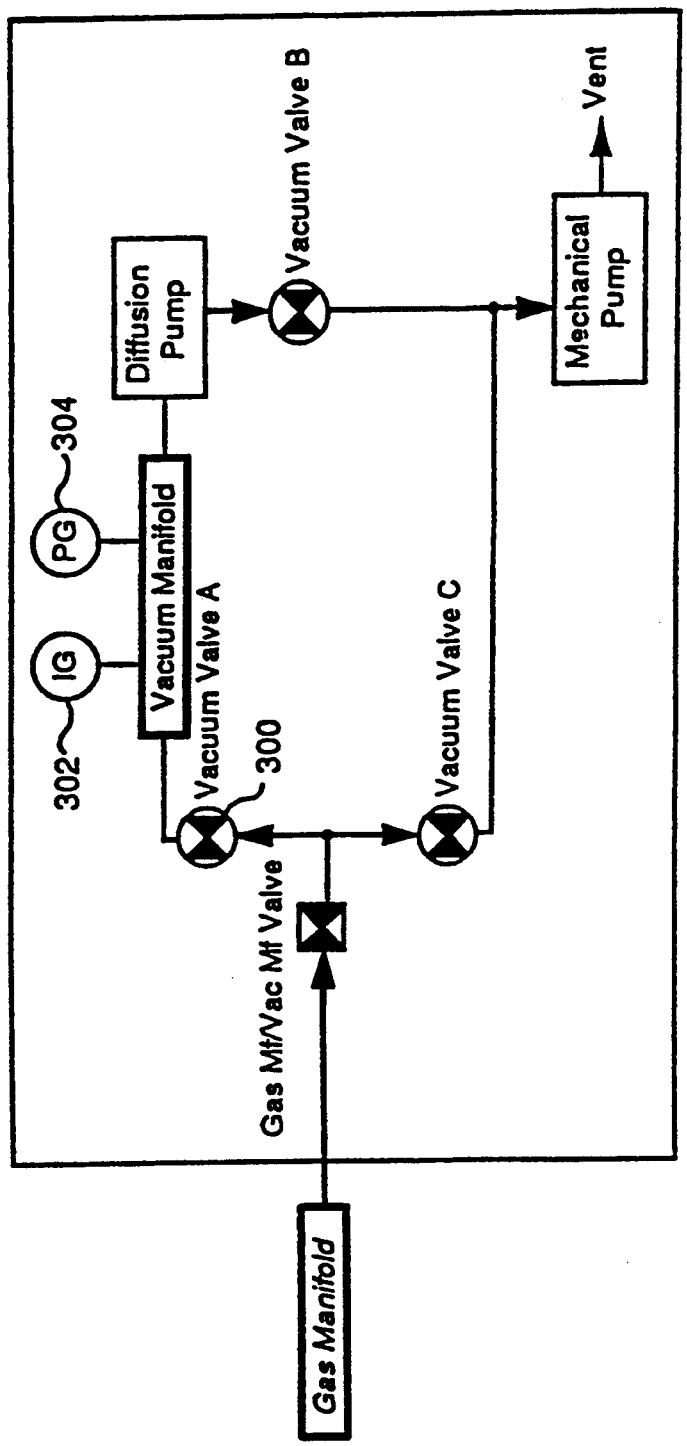
FIG. 10 is a diagrammatic representation of a portion of a preferred embodiment.

In FIG. 10 there is a remotely actuated shutoff valve, 300.

An ionization gauge, 302, designated on the drawing IG.

A pirani gauge, 304 designated on the drawing PG.

Figure 11:
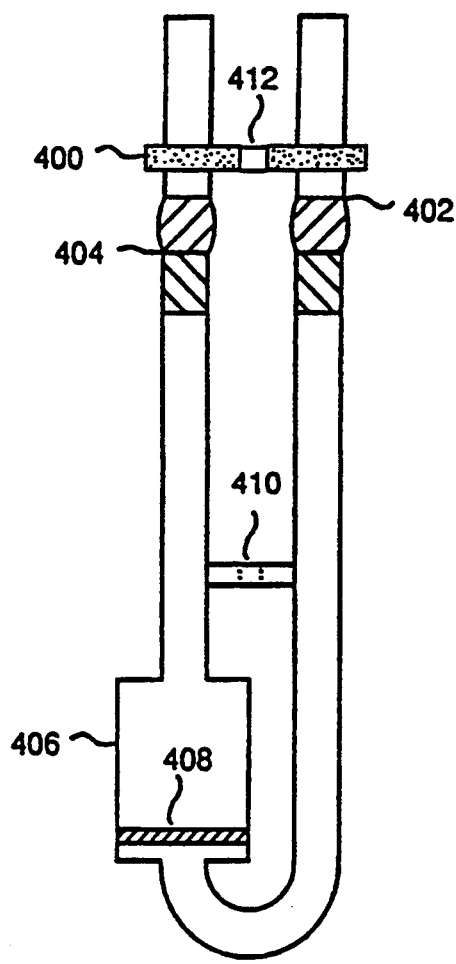
FIG. 11 is a diagrammatic representation of a glass reactor used in a preferred embodiment of this invention.

In FIG. 11 there is a bracket, 400. The bracket holds the metal tubes rigidly.

A glass to metal seal, 402.
A fused quartz to glass seal, 404.
A sample chamber, 406.
A frit of porous fused quartz, 408.
A channel, 410. The channel aids in positioning a thermocouple inserted through the reactor bracket.
A vertical channel and set screw, 412. This is used to position a thermocouple.

Figure 12:
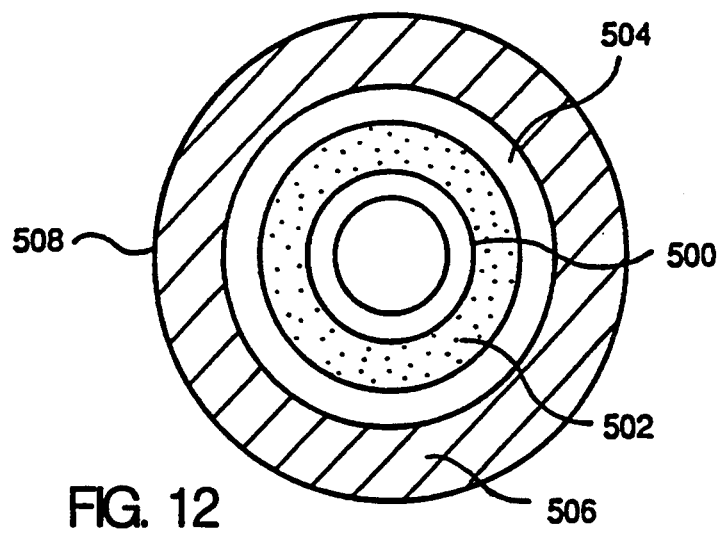
FIG. 12 is a diagrammatic representation of a furnace used in a preferred embodiment of this invention.

In FIG. 12 there is a heating element, 500.
Vacuum cast ceramic fiber insulation, 502.

An annular cavity for the passage of cooling gas, 504.
Outer insulation, 506.
An outer shell, 508.

Figure 13:
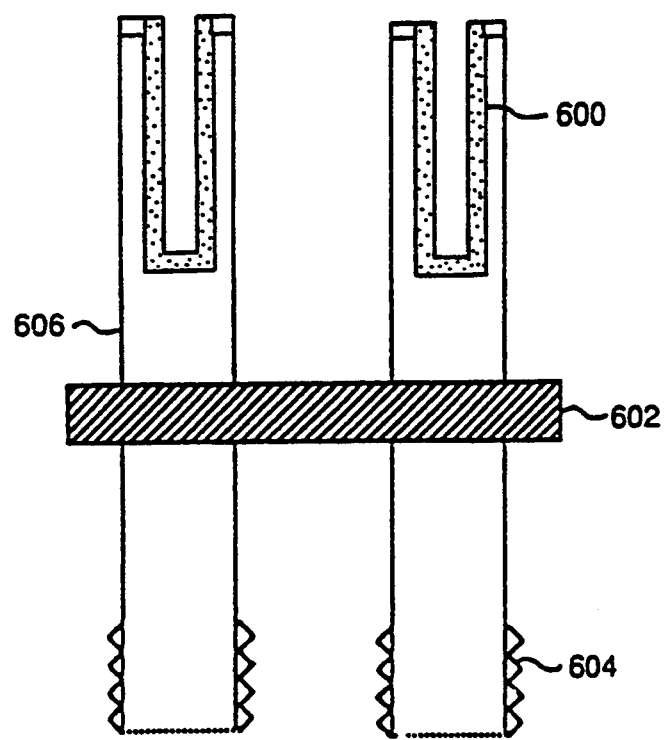
FIG. 13 is a diagrammatic representation of a reactor harness used in a preferred embodiment of this invention.

In FIG. 13 there is an internal filter of large surface area, 600.
    A bracket for rigidly holding the two arms of the Reactor Harness, 602.
    A compression fitting to permit attachment of a reactor which is terminated with a tube, 604.
    A metal tube, 606.

Figure 14:
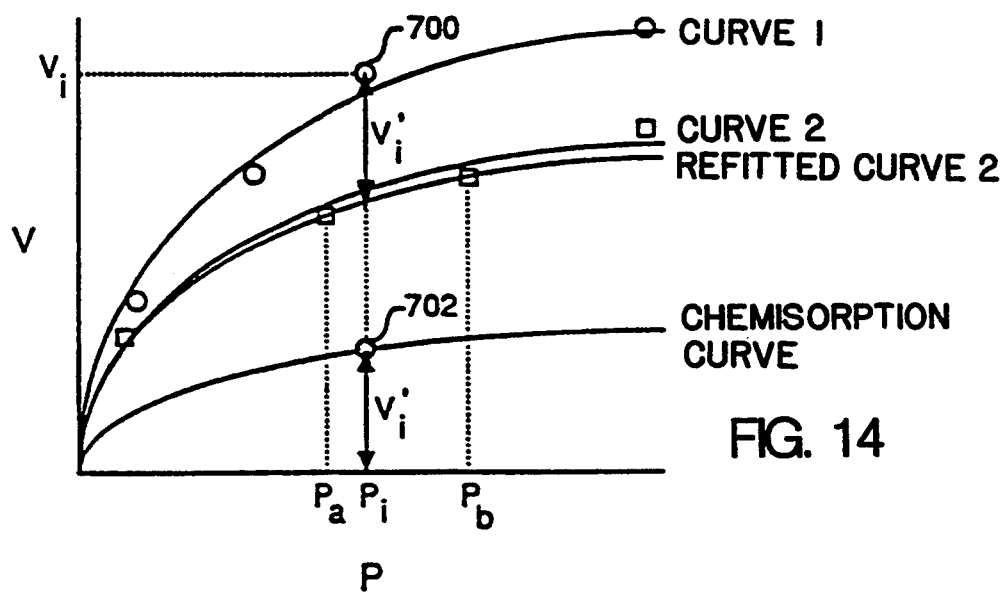
FIG. 14 is a diagrammatic representation of a process for obtaining the amount of chemisorption used in a preferred embodiment of this invention.

In FIG. 14 there is an experimental data point for the amount of adsorption, 700.
    A pseudo data point value for the amount of adsorption, 702.

The apparatus of FIG. 1 has means to accurately measure the amount of gas adsorbed on or desorbed from a solid utilizing the volumetric technique. This apparatus distinguishes from prior apparatus with this means in that this apparatus can also operate at high pressures and can perform and measure chemical reactions of a gas with a solid at low, ambient, and high pressures. This apparatus is a simplified embodiment of the apparatus of FIG. 2 and its operation and use are obvious from the description thereof.

The apparatus of FIG. 2 has means to accurately measure the amount of gas adsorbed on or desorbed from a solid utilizing the volumetric technique. This apparatus is similar to that of FIG. 1 except that a gas analyzer has been added. This apparatus distinguishes from prior apparatus with this means in that this apparatus can also operate at high pressures and can perform and measure chemical reactions of a gas with a solid at low, ambient, and high pressures, and has a gas analyzer suitable for analyzing the effluent from the reactor. This provides means to perform TPC of a solid sample at ambient and high pressures. The vacuum capability also provides means to evacuate gas lines to improve the performance of TPC and shorten the analysis time.

The method of using this apparatus can be readily deduced without undue experimentation by persons skilled in the art once awaare of the present disclosure. Briefly, a solid sample is contained in the reactor. To measure the adsorption of a gas by the volumetric technique, the sample is evacuated and valve 28 is closed. An adsorbate is then admitted to the primary dosing volume bounded by valves 22, 24, 28, and the low pressure transducer 34 and the high pressure transducer 32. Valve 28 is then opened to permit the gas to expand into the reactor. By comparing the drop in pressure to that which occurs for a nonadsorbing gas, usually He, the amount of gas which hall adsorbed on the solid can be calculated. When equilibrium has been achieved, as evidenced by negligible further drop in the pressure, valve 28 is closed. More gas can now be added to the primary dosing volume and the other steps repeated to obtain multiple data points for the amount of adsorption versus pressure.

In a closely related method, an adsorbate isolated within the reactor is permitted to expand into the primary dosing volume. By comparing the drop in pressure to that which occurs for a nonadsorbing gas the amount of gas which has desorbed from the solid can be calculated.

TPC can be performed by flowing a gas over a solid sample and continuously monitoring the effluent with analyzer 42 as the temperature of the sample is raised at a controlled rate. If TPC is being performed at ambient pressure, then a preferred configuration is to have the analyer 42 upstream of the upstream pressure regulating device 36. If TPC is being performed at high pressures, then the same configuration can be used up to the pressure limit of the detector. At higher pressures the configuration depicted in FIG. 2 is used. The upstream pressure regulating device 36 is readily set to control the pressure in the reactor at any value up to its rated pressure. To decrease contamination and shorten the equilibration time of the analyzer 42, prior to the start of TPC the gas lines between valves 22 and 26 can be evacuated.

Chemical reactions can be performed and measured in the flow mode in a manner similar to performing TPC. However, normally the temperature of the sample is kept constant and it is not necessary to continuously analyze the effluent. A common arrangement is to add a gas sampling valve (GSV) downstream of valve 26 to inject a pulse of the effluent into a gas chromatograph. If the reaction is at a pressure below the pressure limit of the GSV, then the GSV can be upstream of the upstream pressure regulating device 36. At higher pressures the GSV is downstream device 36. It is also sometimes desirable to place a gas sampling valve upstream of the reactor 38 so as to enable pulses of gas to be passed over a sample.

Reactions can also be done in the batch mode at pressures substantially below and substantially above 1 atm by using the low pressure transducer 34 or the high pressure transducer 32, respectively, to monitor the pressure of the reaction.

Methodology is also well developed for performing reactions in the flow mode at subambient pressures. Once aware of the present disclosure, without undue experimentation persons skilled in the art could add an evacuation line from the exit of the upstream pressure regulating device 36 and use the output of the low pressure transducer 34 for the input of a control circuit to enable the upstream pressure regulating device 36 to control at subambient pressures. Similarly, the addition of a circulating pump and connections to the apparatus easily permits reactions to be performed in the circulating mode. However, reactions at low pressure and reactions in a circulating system are not of great importance in the field of catalysis.

The apparatus of FIG. 3 has means to perform TPC of a solid sample near ambient pressure. This apparatus distinguishes from prior apparatus with this means in that this apparatus also has means to evacuate gas lines to improve the performance of TPC and lower the analysis time, and means to perform and measure chemical reactions of a gas with a solid at low and ambient pressures. This apparatus is a simplified embodiment of the apparatus of FIG. 2 and its operation and use are obvious from the description thereof.

The apparatus of FIG. 4 has means to perform TPC of a solid sample near ambient pressure. This apparatus distinguishes from prior apparatus with this means in that this apparatus also has means to evacuate gas lines to improve the performance of TPC and lower the analysis time, means to perform and measure chemical reactions of a gas with a solid at low and ambient pressures, and means to accurately measure the amount of gas adsorbed on or desorbed from a solid utilizing tile volumetric technique. This apparatus is a simplified embodiment of the apparatus of FIG. 2 and its operation and use are obvious from the description thereof.

The apparatus of FIG. 5 has means to perform TPC of a solid sample near ambient pressure. This apparatus distinguishes from prior apparatus with this means in that this apparatus also has means to evacuate gas lines to improve the performance of TPC and lower the analysis time, and means to perform and measure chemical reactions of a gas with a solid at low, ambient, and high pressures. This apparatus is a simplified embodiment of the apparatus of FIG. 2 and its operation and use are obvious from the description thereof.

The apparatus of FIG. 6 has means to perform TPC of a solid sample near ambient pressure. This apparatus distinguishes from prior apparatus with this means in that this apparatus also has means to perform TPC at high pressures, and has means to perform and measure chemical reactions of a gas with a solid at ambient and high pressures. This apparatus is a simplified embodiment of the apparatus of FIG. 2 and its operation and use are obvious from the description thereof.

The apparatus of FIG. 7 has means to perform temperature programmed desorption by the direct evacuation method on solid samples of very small surface area. This apparatus distinguishes from prior apparatus with this means in that this apparatus also has means to use samples of very large surface area, the sample is contained in a conventional reactor in contact with air rather than the reactor being inside the evacuated chamber containing the mass spectrometer probe, and this apparatus has means to perform chemical reactions of a flowing gas with a solid at low and ambient pressures.

A method of using this apparatus to perform temperature programmed desorption by the direct evacuation method is summarized as follows. A solid sample in the reactor is exposed to an adsorbate. The reactor is then evacuated and simultaneously the temperature of the sample is raised at a controlled rate and desorbed gas is continuously analyzed by the mass spectrometer probe.

FIG. 8 depicts a gas inlet system used in a preferred embodiment of this invention. Detailed description is contained in a following section. By way of example, inlets for two reaction gases are depicted.

FIG. 9 depicts a reaction system used in a preferred embodiment of this invention. Detailed description is contained in a following section. In order to illustrate certain fluid paths which are unique to an embodiment of the invention which can simultaneously utilize more than one reactor, FIG. 9 depicts an apparatus which can simultaneously use two reactors. The invention can simultaneously use substantially more reactors.

FIG. 10 depicts a vacuum system used in a preferred embodiment of this invention. Detailed description is contained in a following section.

FIG. 11 depicts a glass reactor used in a preferred embodiment of this invention at pressures below about 1 atm. This reactor distinguishes from prior art glass reactors used with apparatus for measuring the amount of gas adsorbed on or desorbed from a solid in that it is highly resistant to breakage, can be attached to a metal coupling without the use of any elastomers, and has a high fluid conductance for evacuation. The metal ends prevent breakage of the open ends of a glass reactor when it is attached to fittings on the Reaction Harness and also allow the use of metal fittings which are much more leak tight and free of degassing than the elastomeric connections which are otherwise required when connecting a glass tube. This increases the accuracy of the apparatus for measuring the adsorption and desorption of gases by the volumetric technique.

The metal ends are held rigid by a reactor bracket which serves to both accurately position the ends of the reactor and to prevent torque, generated when attaching a reactor to the Reactor Harness, from being transmitted to the glass and causing it to break. A preferred reactor bracket alternative embodiment adds a vertical hole 412 in the bracket and a horizontal set screw so to position a thermocouple which extends vertically through the bracket so as to provide means to position the sensing end of the thermocouple next to the sample chamber.

Another alternative embodiment of this reactor adds a channel 410 to help position a thermocouple, said channel being formed by two pieces of fused quartz bridging across the arms of the reactor. Still another alternative embodiment has each open end of the reactor terminated with a fitting suitable for coupling to other fittings. Examples are SWAGELOK, VCR, and VCO fittings.

The preferred size of this reactor is a sample chamber of about 3 to 50 mm I.D., metal tubulation of about 1/16" to 1" O.D., quartz and glass tubing above the sample chamber of about 2 to 50 mm I.D., and quartz and glass tubing below the sample chamber and extending up the opposite arm of the reactor of size about 1 to 20 mm I.D. A more preferred size is a sample chamber of about 3 to 25 mm I.D., metal tubulation of about ⅛" to ½" O.D., quartz and glass tubing above the sample chamber of about 3 to 13 mm I.D., and quartz and glass tubing below the sample chamber and extending up the opposite arm of the reactor of size about 1 to 10 mm I.D.

If the simple is composed of particles of large diameter, then the tubing between the sample chamber and inlet pod of the reactor must be large. However, it is convenient if the reactor harness to which the reactor attaches is for smaller diameter tubing. Another preferred reactor adds a removable reducer to the reactor depicted in FIG. 11. The large end of the reducer is attached to the inlet port of the reactor. The reducer is removed when sample is added to the reactor. The lengths of other tubing on the sample side of the reactor are shortened to offset the added length of the reducer. When the sample being analyzed has a large diameter, it is necessary for the tubing going to the sample chamber to have a large I.D. This can seriously degrade the accuracy of measurements of the amount of gas adsorbed on or desorbed from a solid utilizing the volumetric method. An improvement is to add a glass insert which fills the space above the sample. A preferred insert made of fused quartz tubing of with the ends sealed shut. The insert should be of such diameter that there is about a 0.3 to 1 mm annular space between it and the inner wall of the reactor. For a typical size reactor holding a pellets of a spherical sample of 1 cm O.D., the glass insert will reduce the dead volume of the reactor by about 10 mL and therefore increase the accuracy of the measurements by about 30%.

FIG. 12 is a cross sectional depiction of a furnace used in a preferred embodiment of this invention. For simplicity, pods for the entry and exit of gas are not shown. The furnace depicted is of the tube type, but other types, including a split tube furnace, can also be used. The furnace distinguishes from prior art furnaces used with apparatus for measuring the amount of gas adsorbed on or desorbed from a solid in that it can be heated and cooled very rapidly and can operate at higher and lower temperatures. It is also very light weight and the surface remains cool even when heated to extremely high temperatures, which facilites rapidly removing the furnace. Heating elements are near the inner surface of insulation which is lightweight and of low K factor, which also gives very fast thermal response. A preferred heating element consists of a KANTHAL wire embedded in vacuum cast alumina fiber insulation, providing an upper temperature limit of 1200° C. An alternative embodiment uses a SiC heating element which increases the temperature limit to 1650° C. Between the heating elements and the outer insulation is at least one annular space to which a controlled flow of a gas, typically air or a cryogenic gas, can be directed. The gas enters through a metal tube at the top of the furnace and exits through holes in the bottom. Alternative porting arrangements can also be successfully used.

Both the use of cooling air in an annular space and an ultra light weight insulation to support the heating element is required to achieve exceptional thermal response. The use of only the special insulation gives faster heating than for a conventional ceramic support, but the outer surface of the furnace will become quite hot if the furnace is at temperatures substantially above 500° C. Therefore, in order to avoid using a furnace of large diameter and correspondingly slower response, it is necessary to pass cooling air through the annular space while the furnace is heating. This is sharply distinguished from the common practice of passing air through a furnace in order to cool it after a heating cycle. Further, the use of an inner core of insulation is necessary to shield the hot inner co,re of the furnace and to avoid preferential cooling of a low thermal mass thermocouple in the furnace. The improvement is amplified by also using a fan to blow air against the outer surface of the furnace. Better performance can be achieved by using two annular channels, but this is not normally needed. The inner channel is adjacent to the outer surface of the insulation supporting the heating element. Gas flow in this space serves to quickly cool the heating element. The outer channel is adjacent to the shell of the furnace. Gas flow in this apace maximizes the cooling of the shell. In another alternative embodiment the outer insulation 506 is omitted.

A preferred size for the radial width of the annular space is $\frac{1}{8}$ to 2", and a more preferred size is $\frac{1}{4}$ to $\frac{1}{2}$". The size of a preferred furnace depends on the size of reactor it is to heat. A preferred furnace size suitable for the typical amount of sample (usually 0.1 to 5 g) used for adsorption and desorption measurements is about 4 to 6" O.D. and 7 to 12" long. The use of a cryogenic gas in the air lines allows time programmable temperatures down to −100° C. to be achieved. A preferred source of cryogenic gas is from a tank of liquid $N_2$. An alternative source is compressed $CO_2$.

FIG. 13 depicts a Reactor Harness used to attach a reactor to a preferred embodiment this invention. FIG. 13 is a cutaway view which depicts the internal high surface area filters. The reactor harness enables a means of attaching a reactor to an apparatus. A Reactor Harness can also accommodate a wide range of fittings on each end. The Reactor Harness avoids wear on the fittings of shutoff valves 26 and 28 of FIG. 2 which would otherwise be normally used to attach a reactor and it also traps particulate matter without significantly slowing the evacuation of the reactor or adding dead volume to the apparatus. Slight distortion of the fittings can seriously degrade the vacuum capability of an apparatus, and replacing a valve is much more difficult than replacing the reactor harness.

The reactor harness also contains unusual filters to protect the apparatus against particulate matter without significantly increasing the time necessary to evacuate a reactor. The preferred Reactor Harness consists of two pieces of SS tubing with appropriate end connections. Each side of a Reactor Harness also has a special porous SS filter of large surface area and no dead volume to minimize the chance of particulate matter entering the Reaction Manifold. A preferred Reactor Harness consists of type 316 SS tubing which is between $\frac{1}{8}$" and $\frac{1}{2}$" O.D. and has an internal cylindrical type 316 SS porous filter with a surface area of at least 0.2-sq. in. and a porosity of 0.5 to 100 microns. A more preferred reactor harness consists of $\frac{1}{4}$" to $\frac{1}{2}$" O.D. tubing with an internal filter of surface area 0.3 to 2 sq. in. and a porosity of 5 to 20 microns.

An alternative embodiment adds a port on each arm of the Reactor Harness. A port is normally sealed with a cap, but can be used to provide an additional path for the introduction or removal of solids, liquids or gases from a reactor. The addtion of two ports on one side of the Reactor Harness and a blockage between them enables gas flowing from the Reaction Manifold to exit the apparatus, interact with a variety of external devices including a means of introducing a liquid feed, a gas sampling valve, or a mixing volume, and then reenter the apparatus.

A preferred embodiment of this invention consists of components combined in a novel manner as to achieve the following capabilities. (1) Pressure range of about from $10^{-9}$ torr to 1500 psia. (2) The ability to direct the flow of one or more gases into or through one or more reactors. (3) Time programmable temperature control over the range from about −100° C. to 1200° C. (4) Automatic control of the flow rate of reaction gases. (5) Temperature control down to −196° C. (6) Unusually rapid heating and cooling of a furnace. (7) Ability to automatically raise and lower a furnace or an insulated container about a reactor. (8) Ability to very rapidly switch between the use of a furnace and insulated flask, thereby achieving unusually rapid cooling of a reactor since it is not necessary to also cool the furnace. (9) Accurate measurement of the pressure in the each of the ranges of about 0 to 1000 torr and 0 to 1,500 psia. (10) Unusually high accuracy for measuring the amount of gas adsorbed on or desorbed from a solid utilizing the volumetric technique. (11) Unusually fast evacuation of a reactor. (12) Remote actuation of the vacuum valves. (13) Ability to use solid samples of surface area from about 0.01 to 1500 m²/g, powders, porous solids, and sample sizes of about 1 mg to 200 g. (14) Protection of the valves from particulate matter achieved without significant affect on the pumping speed of the apparatus. (15) The ability to individually control and measure the flow of a reaction gas in each of a plurality of reactors through which it is simultaneously passing. (16) The unusual ability to rapidly switch the pressure of a reaction gas from 1 atm to high pressure. (17) The ability to attach a glass reactor to the apparatus without breakage or the introduction of elastomeric materials. (18) The unusual ability, to easily test the system for leaks and enable the safe use of shutoff valves which are plumbed in a backwards manner. (19) The capability to analyze the reactor effluent. (20) Easy modification and maintenance of the apparatus. (21) Improved process for obtaining chemisorption measurements. (22) Improved reactors. (23) Capability to do TPC. (24) The ability to perform measurements unusually fast.

A detailed description of a preferred embodiment of the present invention follows. The complex arrangement of components can be simplified by considering the machine to be composed of systems and manifolds. A system is defined as a major group of components that act together as a unit. A manifold is defined as an elongated conduit for the transport of gas which interconnects a number of components. For each of the FIG. 8 through 10, lines and arrows show the normal direction of gas flow. A small arrow next to a valve indicates that the valve is plumbed in a direction opposite to that normally done. Parts outside of the rectangle are included to help show the interrelationship of the systems.

A preferred embodiment consists of five systems: Gas Inlet System, Reaction System, Vacuum System, Analyzer System, and the Computer System. Each manifold is contained within a system and is described therein.

The Gas Inlet System, FIG. 8 accepts gas from a supply and directs it to the appropriate manifold. The Gas Inlet System also controls the flow rate of gases which enter the Gas Manifold. Metal tubing used in the preferred embodiment is SS. Tubing and fittings with a pressure rating of 10,000 psia are readily available, for example from the Swagelok Co. of Solon, Ohio. In an alternative embodiment, any of a large number of other metals can be used which are well known to those skilled in the art. This includes less common materials such as TEFLON lined SS and glass lined SS.

A check valve 104 is attached to the inlet side of the shutoff valve for each reaction gas. A preferred check valve is constructed of type 316 SS, has a VITON seat, and has a pressure rating of at least 1500 psia.

A packed shutoff valve 102 is directly attached to each reaction gas supply. Three additional valves control the gas supplies for the Furnace Air, Valve Air, and Back Pressure Regulator (BPR) Manifolds. The valves for the reaction gases are redundant, since another valve is supplied for each gas which enters the Gas Manifold. These extra valves are provided for safety and as an aid in leak testing. These valves enable bellows valves to be safely plumed in a novel and backwards direction, which substantially improves the performance of the machine with respect to the speed of evacuation and the accuracy of measuring the adsorption and desorption of gases. A preferred shutoff valve is constructed of type 316 SS with a Teflon packing and has a pressure rating of at least 1500 psia.

The rate of flow of a reaction gas entering the Gas Manifold is preferably controlled by a mass flow controller 100 (MFC). A preferred MFC is constructed of type 316 SS with VITON O-rings has a pressure rating of 1500 psia, is tested to have a leak of $<4\times10^{-9}$ mL (STP)/s, and has a flow capacity suitable for the processes to be monitored. MFC are commercially available which can control flow from $8\times10^{-4}$ to $1.6\times10^3$ mL (STP)/s. in some applications equally good performance can be achieved using a metering valve. A preferred metering valve is constructed of type 316 SS with a VITON packing, has a pressure rating of 1500 psia, and has a flow capacity suitable for the processes to be monitored. At this time the highest pressure rating of an MFC is 3500 psi. An example is model 5850E manufactured by Brooks Instrument of Hatfield, Penn.

A bellows shutoff valve 110 controls the entry of each reaction gas into the Gas Manifold. Bellow valves have extremely low leak levels. A bellows shutoff valve has a direction of gas flow stamped on the body by the manufacturer. This directionality arises as a safety feature, since the bellows is the weakest part of the valve and is exposed to the upstream gas supply even when the valve is closed. However, examination of the insides of such a valve reveals that almost all of the internal volume is contained on the side of the valve seat having the bellows. The total internal volume of a preferred bellows valve is about 1 to 4 mL. Therefore, plumbing a bellows valve backwards results in a substantial reduction in the volume of the manifold to which it is connected. Lowering the internal volume of a manifold proportionately increases the accuracy of adsorption and desorption measurements and reduces the time to evacuate the manifold. A preferred embodiment of the invention has each of the bellows type valves for reaction gases which are attached to the Gas Manifold plumbed in a backwards direction. This novel configuration can be safely done due to the presence of redundant shutoff valves upstream of the bellows valves. The preferred bellows valve is constructed of type 316 SS, has a stem tip of SS, and has a pressure rating of at least 1500 psia. An example of such a valve is model 4A-P4R-SS manufactured by the Parker Corp. of Huntsville, Ala. An alternative preferred valve is remotely actuated. Such valves are compatible with computer controlled operation. An example is the HB series valves manufactured by the Nupro Co. of Willoughby, Ohio.

The Gas Manifold is a piece of narrow bore SS tubing to which various components are attached. A preferred Gas Manifold is constructed of type 316 SS tubing of ⅛ to 1" O.D. and has a pressure rating of at least 1,500 psia. A more preferred Gas Manifold is constructed of tubing in the range of 0.25" O.D.×0.15" I.D. to 0.5" O.D.×0.3" I.D.

An accurate high pressure transducer 112 is attached to the Gas Manifold and continuously monitors the pressure in the Gas Manifold. A preferred HPT is a capacitance type gauge constructed of SS of low internal volume (<10 mL) with a range of 0 to 1500 psia and an accuracy of 0.1% of furl scale. An example is model 204 manufactured by Setra Systems Inc. of Acton, Mass. A preferred embodiment of the invention uses the output of the HPT as part of a circuit which will activate an alarm if the pressure exceeds 1,500 psia. In an alternative embodiment of this invention, this high pressure transducer or a second one is placed downstream of the reactor. High pressure transducers with a range up to 10,000 psia are available from Setra Systems.

Air which passes through the Furnace Air Valve 114 enters the Furnace Air Manifold. As a safety feature, a pressure gauge 106 continuously displays the pressure in the Furnace Air Manifold. A preferred Furnace Air Manifold is constructed of brass of approximately 0.5" O.D.×0.2" I.D. and has a pressure rating of at least 100 psia.

Air which passes through the Valve Air Valve 116 enters the Valve Air Manifold which then directs the air to a control valve to actuate a vacuum valve. As a safety feature, a pressure gauge continuously displays the pressure in the Valve Air Manifold.

A preferred Valve Air Manifold is constructed of brass of approximately 0.5" O.D.×0.2" I.D. and has a pressure rating of at least 150 psia.

Opening the BPR Pressurize Valve 118 admits the gas used to set the reference pressure of the BPR to the BPR Manifold and to the regulating dome of the BPR.

A tube also goes to the BPR Reference Pressure Gauge which continuously displays the pressure in the BPR Manifold. A preferred BPR Manifold is constructed of copper, brass, or SS of 1/16" to ¼" O.D. and has a pressure rating of at least 1,500 psia.

Numerous conventional porous metal disc type filters 102 are present in the Gas Inlet System. A preferred filter is constructed of type 316 SS and is of 0.5 to 50 microns porosity. The most preferred filter is of porosity 1 to 20 microns.

The Reaction System, FIG. 9 accepts gas from the Gas Manifold and directs it to the appropriate reactor and vent. The Reaction System also controls the pressure of reaction gases within the machine, controls the temperature of reactors, and provides very accurate measurement of the pressure in the Reaction Manifold in the range of 0 to about 1000 torr.

The Reaction Manifold is a piece of narrow bore SS tubing to which various components are attached. A small I.D. of the Reaction Manifold is preferred in order to lower its internal volume and thus increase the accuracy of adsorption and desorption measurements. However, a small I.D. slows evacuation. A clever choice so as to minimize the internal volume without significantly increasing the evacuation time is to have the I.D. of the Reaction Manifold about 60% of the I.D. of the Gas Manifold. A preferred Reaction Manifold is constructed of type 316 SS tubing of size ⅛ to 1" O.D. and has a pressure rating of 1,500 psia. A more preferred Reaction Manifold is constructed of tubing of size 0.25" O.D.×0.06" I.D. to 0.5" O.D.×0.3" I.D.

A very accurate low pressure transducer 202 (LPT) is provided to measure the pressure in the Reaction Manifold in the range of about 0 to 1000 torr. A preferred LPT has a low internal volume (<10 mL), is constructed of SS and an accuracy of at least 0.1% of FS. A more preferred LPT has an accuracy of from 0.02% to 0.15% of reading. An example is the model 390 manufactured by MKS of Andover, Mass. An alternative embodiment is to use two or more LPT's so as to achieve higher accuracy in the low pressure range. Extremely accurate LPT's with full scale ranges of 1, 10, 100, and 1000 torr are manufactured by MKS.

The low pressure transducer will be damaged if the pressure to which it is exposed exceeds about 1250 torr. For this reason it is protected by the LPT Isolation Valve. The preferred embodiment of the invention uses the output of the HPT as the input of an electronic circuit which will activate an alarm if the pressure exceeds 1,000 torr. This warns the operator to close the LPT Isolation Valve. Such circuits are well known to those skilled in the art of electronics. The preferred and alternative LPT isolation valves are a bellows type valve as described previously.

A variety of valves direct the flow of the reaction gases. The Gas Manifold/Reaction Manifold Valve is a supplemental valve which separates the two manifolds. This novel implementation lowers the volume of gas whose pressure is being measured by the LPT by about 2-fold, and consequently increases the accuracy of adsorption and desorption measurements made by the volumetric technique by about 2-fold. It also enables an unlimited number of gas pens on the Gas Manifold without affecting the accuracy of such adsorption measurements. This valve is also plumbed in a backwards direction, which further reduces the volume of gas in the Reaction Manifold and provides advantages previously described.

The presence of the Gas Manifold/Reaction Manifold Valve adds additional mechanical and data acquisition steps to the normal sequence for adding a dose of gas to a reactor. This valve is first opened so gas can be added to the primary dosing volume. When the desired pressure is achieved, gas flow is stopped and the valve is closed. This will perturb the pressure, so a new pressure reading must be taken. The dose is now added to the reactor in the normal manner. After recording t, he equilibrated pressure the valve is again opened and the process repeated.

It has been noted that it can be difficult to deliver small doses of gas to a reactor. This is especially true if the apparatus is automated and the pressure in the dosing volume is low. Such small doses are rarely needed, but in some cases, such as measuring microperosity, is useful. In a alternative embodiment of the present invention, a secondary dosing volume is added to enhance this capability. The secondary dosing volume is of size <5 mL, and preferably about 1 mL. It is bounded by two valves. The first valve isolates the secondary dosing volume from the first dosing volume. A third valve, fourth valve, and low pressure transducer are connected to the opposite side of the second valve. The third valve is connected to a gas supply and the fourth valve is connected to vacuum. To use the secondary dosing volume, a known pressure of gas is added. The second valve is then closed, and the first valve is opened to expand the gas into the primary dosing volume and reactor. When equilibrium is achieved, the first valve is closed, the pressure in the secondary dosing volume is increased, and the process is repeated.

Still another alternative embodiment of the invention solves this problem by adding a valve and secondary path to vacuum which is of low fluid conductance and in parallel with the path provided by valve 24. If the pressure in the dosing volume is too high, the pressure is reduced in a slow and controlled manner by evacuating with the secondary path. Evacuation with the primary path in a well designed apparatus can cause the pressure to drop from 760 torr to 1 torr in about 2 s, which is much too fast to control. At pressures below about 0.01 torr the speed of evacuation is slow enough that the pressure can be set using the primary path of evacuation. The conductance of the secondary path depends on the size of the primary dosing volume. It is adjusted to give a rate of evacuation of roughly 0.1 torr/s at a pressure of 1 torr. For finer control, a variable conductance valve or multiple secondary paths can be used.

A Bypass Valve provides a fluid path to vent without passing through one of the reactors. The Bypass valve is used to establish baseline conditions of flow and analyzer before starting a flow gas through a reactor. Gas flowing through the Bypass valve can be directed either to the BPR or to Vent.

Each shutoff valve 214 attached to a reactor harness provides means for gas to flow from the Reaction Manifold into a reactor. A metering valve 216 on the exit of each reactor provide means for gas which is simultaneously flowing through more than one reactor to be partitioned in any ratio between the reactors. A 3-way valve 208 provide an unusually rapid means of controlling whether the effluent will be to a vent or through the BPR. A preferred valve and alternative embodiments for the Gas Manifold/Reaction Manifold Valve, Bypass Valve, and the two valves proximate to a reactor are bellows type valves as described previously. A preferred metering valve and alternative embodiments are as previously described. The preferred 3-way valve is constructed of type 316 SS with a Teflon packing and has a pressure rating of 1500 psia. It is to be noted that in a preferred embodiment of this invention all valves which are in fluid communication with a sample during a measurement of adsorption or desorption of gas by the volumetric method are packless.

A preferred embodiment of the present invention utilizes shunts to help control the flow of gas. A shunt is here defined as a readily removable piece of tubing suitable for gas flow. A preferred shunt is made of 1/32" to ½" O.D. tubing, and most preferably is 1/16" to ⅛" O.D. A preferred shunt is made of SS or other material appropriate to the gases being handled. It is preferred that the shunt be connected to ports with easily removable fittings, such as Swagelok compression fittings or Swagelok Quick-Connects.

The use of shunts can be exemplified by reference to FIG. 9. Two shunts could be used to connect the Reactor 1 Vent and the Reactor 2 Vent to the sample sides of two TCD's, thereby providing the necessary sample flow paths to perform simultaneous TPC. A more complex use is to provide means for a single GSV to function in both a downstream and upstream mode with respect to the reactor. A preferred GSV is the common six port, three groove design. In a preferred embodiment of the present invention a Reaction gas line, as depicted in FIG. 8, is opened downstream of its flow control device and upstream of the reactor, and most preferably upstream of the Gas Manifold. It is most preferable if the open ends are terminated in convenient fittings, such as bulkhead Swagelok fittings which are mounted so as to be readily accessible. If a shunt connects the two open ends, there is no change in flow path. In this case another shunt can connect the vent pert of a reactor to an inlet port of a GSV, so that the sample loop of the GSV can send pulses of the reactor effluent to an analytical device. On the other hand, separate shunts can be attached to the two open ends of the gas line and the other ends of the shuns attached to the GSV. In this case the GSV can cause pulses of a different gas contained in its sample loop to enter the reactor.

A Reactor Harness 200 is attached to the pair of inlet and outlet valves which are proximate to a reactor. A preferred Reactor Harness is depicted in FIG. 13.

A large variety of glass and metal reactors can be attached and removed from the apparatus. A preferred choice of reactor depends on the type of measurement being made. chemisorption measurements, TPC, and many reactions are normally done in a flow-through reactor. A preferred glass reactor for chemisorption measurements is shown diagramatically in FIG. 11. If measurements of the adsorption or desorption of gas with a solid are being performed, then a preferred volume is 0.5 to 50 mL, and a more preferred volume is 1 to 20 mL. A bulb type reactor having a common port for the entry and exit of gas is commonly used for physisorption measurements. These are well known to those familiar with the art of physisorption measurements.

A common type of metal reactor is straight and tubular. It is common in apparatus for measuring the adsorption of a gas to need to put a cryogenic bath about a reactor, so the tubular shape is not practical. A preferred metal reactor has a shape similar to that depicted in FIG. 11, is constructed of 316 SS, and has a pressure rating of 1500 psia. Since the reactor is metal, the glass to metal seal 402 and the quartz to glass seal 404 are not used. The porous glass disc 408 is replaced with a porous SS disc, SS wire screen, or a wad of glass wool. The metal tubes are welded together. Another improvement of the preferred reactor is that the tubing in the outlet side of the reactor is of narrow bore, thereby improving the accuracy of measurements of gas adsorption If the sample particles are large, then a reducer fitting can be added to the reactor as previously described for a glass reactor.

A preferred embodiment of the present invention adds a glass liner to a metal reactor. The liner serves to minimize side reactions, makes it easier to load and clean the reactor, and helps support a solid sample. The liner is preferably constructed of fused quartz or a similar material aid contains a porous frit to support a catalyst. The liner preferably has a wall thickness of about 1 mm and fits snugly within the reactor. The bottom of the liner rests on a restriction in the inner diameter of the reactor. The restriction can be in the body proper of the reactor or in a removable fitting attached to the exit port of the reactor. To avoid gas flow in the annular space between the liner and the reactor wall, a gasket seals the annular opening which is near the inlet port of the reactor. It is not necessary to likewise seal the bottom end of the liner, as there is no dynamic flow of gas in the annular space and it is necessary to provide for the equilibration of gas pressure in the annular space if the reactor is used at high pressure. The gasket is preferably an O-ring of inner diameter equal to the inner diameter of the liner, and of outer diameter equal to the inner diameter of the reactor. The O-ring rests on top of the liner and is slightly compressed by a compression fitting on top of it. The fitting is preferably a metal annulus. The compressive force can arise in various ways, including having the fitting threaded and screwed inside of the reactor. A preferred compression fitting extends about 0.2 mm above the top of the reactor, so the O-ring is compressed when the top of the reactor is attached to the reactor harness.

An improvement of this invention is that almost any laboratory scale reactor can be attached to the Reactor Harness by using metal tubing and fittings. Examples of such alternative embodiments are a tubular reactor, stirred autoclave, continuous stirred tank reactor, BERTY reactor, fluidized bed reactor, and slurry reactor. Such reactors are manufactured by a variety of companies including Parr Instruments of Moline, Ill., and Autoclave Engineers of Ede, Penn.

A furnace used with a preferred embodiment of this invention is depicted in FIG. 12. The furnace is of novel design, having means for extremely fast heat up and cool down. A fan blows a high volume of air across the outer surface of a furnace, thereby greatly lowering the surface temperature from what it would otherwise be. At high temperatures, a flow of air is also passed through an annular space to further lower the shell temperature. The fan and internal air flow therefore allow a furnace to be constructed with much less insulation and hence much smaller thermal mass than would otherwise be possible. A preferred embodiment of the invention uses a fan with an air flow of about 20 to 250 cfm, and a more preferred embodiment uses a fan with an air flow of about 70 to 150 cfm.

A preferred embodiment of the invention utilizes a novel combination of two different gas flows to the annular space of a furnace, each controlled by a remotely actuated valve. One flow is smaller, termed Slow Air, and the other is larger, termed Fast Air. A flow of Slow Air can be continuously maintained during a heating cycle and serves to further lower the outer skin temperature of a furnace, providing the advantage previously described. The Fast Air flow can further enhance this effect and is especially used to greatly increase the rate of cooling of the furnace. In the preferred embodiment of this invention the gas flows are remotely controlled by the second output of a dual output temperature controller. This output can have proportional control, thereby minimizing temperature overshoot which allows unusually high rates of heating to be controlled and permits temperature programmed cooling. A preferred ratio of the rate of Fast Air flow to Slow Air flow is 1:1 to 10:1, and a more preferred ratio is 2:1 to 4:1. A preferred rate of flow for the Fast Air is 0.5 to 20 cfm, and a more preferred rate of flow is 3 to 10 cfm. Cryogenic gases, such as the boil-off from liquid $N_2$, can be used to achieve subambient temperature programming down to $-100°$ C.

The apparatus can also contain other regions which are maintained at a constant temperature. It is especially preferable to thermostat the low presssure transducer and the Reaction Manifold. Such additional heated zones can slightly increase the accuracy of adsorption and desorption measurements made by the volumetric method and can reduce the time to degas the apparatus. A platform 210 supports a furnace or an insulated flask and provides means for the temperature controlled zone to be raised or lowered about a reactor. The platform is remotely raised and lowered using a pneumatic piston. This design enables very rapid switching between the use of a furnace and insulated flask for temperature control.

Electropneumatic valves 204 and 206 are attached to the Furnace Air Manifold to control the flow of cooling air to furnaces and to position the pneumatic platforms. The valves are remotely actuated. Valves are widely available for noncryogenic gases. An example of a preferred valve for the flow of a cryogenic gas is model SV-91 and is rated for service at $-196°$ C.

A temperature controller is provided for each furnace. A preferred temperature controller is a microprocessor controlled unit, has proportional, integral, and derivative control, is multilevel programmable, and has dual outputs. Programmable control allows the temperature controller to change the temperature of a reactor at set rates. Dual control allows the temperature controller to simultaneously control both a heating current and cooling gas flow to a furnace, thus providing means for time programmable cooling. An example is model CN8622 made by Omega Engineering of Stamford, Conn. An alternative embodiment uses a temperature controller which is interfaced to a computer so as to be able to remotely controlled. An example is model CN2042 made by Omega Engineering.

The novel arrangement of vents and components downstream of the reactors provide an improved degree of flexibility in the apparatus. A separate vent for each reactor, the Bypass Valve, and the BPR is provided. Each vent includes a connector, which provides means to quickly connect a shunt. Separate vents and metering valves for each reactor provide means to individually control and measure the flow rate through each reactor when gas is simultaneously passing through more than one reactor. A separate vent for the BPR provides means for a BPR/Vent Selector 3-way valve to enable unexpectedly quick switching between gas flow at ambient and high pressure. Another improvement of the apparatus is that when operating at high pressure, added flexibility is achieved by not having the gas flow from a reactor directly enter the BPR, but is directed to the BPR Feed port. In a preferred embodiment, a shunt connects the BPR Feed port to the BPR In port. In an alternative embodiment, the shunt is replaced with other devices such as a cold trap to remove condensable substances from the gas flow or a GSV. A preferred vent consists of a bulkhead union constructed of 316 SS.

The BPR 212 is an upstream pressure regulating device which isolates the pressure of gas upstream from it from atmospheric pressure, thereby allowing a reaction to be run at elevated pressures. Opening the BPR Pressurize Valve increases the setpoint of the BPR. The BPR Vent Valve allows the setpoint pressure in the BPR to be reduced down to 1 atm. A preferred BPR is of the dome loaded type, is constructed of type 316 SS with a VITON diaphragm, has an internal volume to which the reaction gas is exposed of <10 mL, and has a pressure rating of 1500 psia. An example is model 90W manufactured by Grove Valve & Regulator Co. of Oakland, Calif. Alternative embodiments are a spring loaded BPR, a reverse acting mass flow controller such as manufactured by Brooks Instrument, Hatfield, Pa., and a control valve such as manufactured by Badger Meter, Inc, of Tulsa, Okla. Another alternative embodiment utilizes a remotely controlled upstream pressure regulating device. Automatic operation of a dome loaded BPR, reverse acting MFC, and control valve is readily achieved by those skilled in the art of gas flow. Both manually and remotely controlled upstream pressure regulating devices are available with a pressure rating of 10,000 psia.

The Vacuum System, FIG. 10, consists of those parts necessary to maintain and measure the vacuum. The Vacuum System evacuates gas from the Gas Manifold and displays the pressure of the Vacuum Manifold.

The Vacuum Manifold consists of a piece of wide bore SS tubing to which various components are attached. A preferred Vacuum Manifold has an I.D. of about from $\frac{1}{2}$ to 8" and has a volume of about 0.3 to 20 L. A more preferred Vacuum Manifold has an I.D. of about 2" to 5" and has a volume of about 0.5 to 5 L. The Vacuum Manifold deliberately has a large volume so as to substantially shorten the time necessary to rough evacuate the Reaction Manifold prior to evacuating in the high vacuum mode.

The bellows type Gas Manifold/Vacuum Manifold Valve separates the Gas Manifold from the Vacuum Manifold. Vacuum Valve A 300 and Vacuum Valves B and C control the path of an evacuation and are remotely actuated. Rouch evacuation is through Vacuum Valve C. Unusually fast evacuation is achieved by first evacuating the Reaction Manifold until the pressure is about 1 torr. The pumping is now switched to the high vacuum mode via Vacuum Valves A and B. Expansion of the residual gas into the much larger volume of the Vacuum Manifold serves to both protect the high vacuum gauge and rapidly lower the pressure in the Reaction Manifold, A preferred valve for Vacuum Valves A and C is of the bellows type as previously described. A preferred valve for Vacuum Valves B is similar except that the preferred range of tubulation size is about 0.5 to 1".

A preferred high vacuum gauge is an ionization gauge 302 with a pressure range of about $1 \times 10^{-2}$ to $1 \times 10^{-10}$ torr, and includes a digital readout of the pressure. The filament in an ionization gauge will burn out if exposed to pressures above about 0.01 torr. A preferred ionization gauge also includes Circuitry to automatically turn off the gauge if the pressure is $>0.01$ torr. An example is model IG3 made by Inficon of East Syracuse, N.Y.

The Pirani gauge 304 is directly attached to the Vacuum Manifold. The gauge reads the pressure of the Vacuum Manifold in the range of about $1 \times 10^{-4}$ to 600 torr. In a preferred embodiment of the invention, this gauge is part of the circuitry to detect an over pressure error If the pressure in the Vacuum Manifold exceeds about 0.1 torr, a circuit removes power from the diffusion pump to keep it from being damaged. A preferred Pirani gauge is constructed of SS. An example is the MODUCEL gauge made by MKS of Boulder, Colo.

The diffusion pump is directly attached to the Vacuum Manifold and evacuates it to a low pressure, achieving an ultimate vacuum of $10^{-9}$ torr. A preferred diffusion pump is constructed of SS, has a pumping speed of from 30 to 500 L/s, has an internal water cooled optically opaque baffle, and can achieve an ultimate vacuum of at least $10^{-8}$ torr. An alternative embodiment uses a turbomolecular pump.

The mechanical pump reduces the pressure in the Vacuum Manifold to a pressure low enough to enable the diffusion pump to work. A preferred mechanical pump is of the two stage design, can achieve an ultimate pressure of about $1 \times 10^{-3}$ torr, and has a pumping speed of about 25 to L/S.

In a preferred embodiment of the present invention, the Computer System provides means to calculate, display, store, print, and recall data. The Computer System also acquires and treats data during TPC. The Computer System includes a computer, appropriate software, and circuit boards which provide means for A/D (analog to digital) conversion, D/A (digital to analog) conversion digital I/O (input/output) signals, and timers. A preferred A/D board provides 12 bit resolution and software programmable gain. Solid state relays interlace the output of the digital I/O board to electropneumatic control means. If used, a mass spectrometer is also controlled by the Computer System. It is preferred that the output of a 12 or 14 bit D/A board be used to drive the scan of the mass spectrometer. In another preferred embodiment, additional software enables all valves to be operated via the computer, and pressure, temperature, and flow to be controlled and measured by the computer. A wide choice of computer systems utilizing personal computers is readily available. The required computer boards and software are readily available from a variety of vendors. An example is products of National Instruments of Austin, Tex.

The Analyzer System contains means to at least partially analyze the composition of the effluent from a reactor. The Analyzer System consists of (1) components necessary for the detector to be in fluid communication with the effluent of a reactor and (2) an analyzer which contains a detector in fluid communication with the reactor. The choice of analyzer, its placement in the apparatus, and the means of fluid communication depend on the particular measurement being made.

A preferred Analyzer System for analysis of chemical reactions when neither adsorption nor desorption measurements are needed consists of a GSV which is downstream from a vent and directs pulses of the reactor effluent to a gas chromatograph analyzer. A preferred Analyzer System for TPC consists of a SS shunt connecting a reactor vent to a TCD. Alternative preferred analyzers for this Analyzer System are a flame ionization detector, ultrasonic detector, gas density balance, ionization detector, and infrared spectrometer. Each of these alternative analyzers are known to those skilled in the art. An alternative preferred Analyzer System for the analysis of the reactions of gases with solids consists of (1) a molecular leak downstream from a vent so as to provide a means to transport a small quantity of the reactor effluent to an evacuated chamber containing a detector, and (2) a mass spectrometer analyzer. The preferred analyzer for performing temperature programmed desorption by the direct evacuation method is a mass spectrometer detector inside of the Vacuum Manifold.

A preferred embodiment of the present invention has TPC capability. A preferred gas analyzer is a TCD. It is preferred that separate gas streams be used for the sample and reference side of the TCD, rather than the conventional series mode. This enables much of the tubing in fluid communication with the TCD to be evacuated prior to introducing the reaction gas used for TPC so as to lower the, equilibration time of the TCD. The parallel mode is also necessary for simultaneous TPC. In a preferred embodiment, this mode is achieved by adding a tee upstream of the shutoff valve for the reaction gas in the gas inlet system and directing a flow of this gas through a flow control device and into the reference side of the TCD.

The equilibration time of the TCD can be significantly shortened by evacuating gas lines of any previous gas and then introducing the new reaction gas for TPC. Evacuation is much faster than purging. In the parallel mode of operation, the amount of gas in the gas lines going to the reference side of the TCD is so small that purging is acceptable for the reference side. However, due to the relatively large volume and presence of nonswept volume in the reactor and tubing upstream of it, it is preferred that this volume be evacuated. Even faster equilibration can be achieved in an alternative embodiment of this invention wherein another valve is added downstream of the reactor and preferably on the vent of the sample side of the TCD. This enables all of the gas lines connected to the sample side of the TCD to be evacuated.

Usually a sample is first pretreated, in which case the TCD should be equilibrated at the same time. A shunt (or selector valve and tubing) then directs the effluent from the reference side into the sample side. When TPC is started, the shunt is removed and gas is supplied to the sample side of the TCD from a separate stream via a shunt connecting a reactor vent to the TCD.

It is also preferable that the thermal equilibration time of the TCD be shortened by using a multilevel current profile. Assuming that the current at which the TCD will operate during TPC is i, then the current is first set to a value of about 1.5 to 2 times i and drift of the TCD is monitored. When the drift equals the amount previously found by having the TCD equilibrate at current i, the current is set to the value i. The TCD is now at its asymptotic value of drift, and further drift is extremely low. After performing this process once, the change in current can occur at a set time without monitoring the amount of drift.

Another preferred embodiment of this invention adds a flow snubber downstream of a reactor and upstream of a TCD. Many forms of snubber are available, a preferred snubber being about a 4" long×¼" O.D. piece of SS tubing filled with about 80 mesh glass beads. The snubber improves the accuracy of TPC by smoothing flow perturbations and slightly broadening sharp peaks, especially those caused by a gas sampling valve when the response of a TCD is calibrated.

Another preferred embodiment of this invention adds a flow measuring device, such as a bubblemeter, downstream of a reactor and measurements of the flow through the sample side of the TCD are made during TPC. The use of this true detector flow, rather than the flow controlled by the flow control device upstream of the reactor, provides for more accurate measurement of the amount of gas which has reacted during TPC.

When TPC is performed with the present invention utilizing a TCD, an unusually stable baseline is observed. Therefore, temperature programmed reduction can be done at unusually high concentrations of hydrogen in argon and still retain acceptable sensitivity. An unexpected result is that since the thermal conductivity of the gas mixture with high concentrations of hydrogen is substantially higher than that for a normal mixture, then the TCD can be operated at higher currents. This significantly increases the sensitivity of the TCD and substantially offsets the reduced sensitivity caused by the high concentration of hydrogen.

The preferred method of data acquisition is with an analog to digital (A/D) converter having software programmable gain. Software acquires the signal from the TCD and automatically ranges the A/D converter to provide maximum resolution and wide dynamic range. A preferred A/D converter has 12 bit resolution and full scale ranges from about 20 mV to at least 1 V. This provides the surprising result that good resolution is achieved over the entire signal range and even large signals will not go offscale.

The process of acquiring the raw signal from a TCD profoundly affects the sensitivity and accuracy of the TPC results. It has been noted that typical noise rejection is done by a low pass 60 Hz filter, and gas pulses used to calibrate the response of a TCD are normally quite sharp. Detailed analysis of the peculiar experimental characteristics of TPC of granular samples, which includes almost all catalysts, reveals the unexpected result that much more signal averaging can be done without distorting the data. The thermal conductivity of granular matter is low, and as a result heating rates during TPC must be modest, typically less than 30° C. It is also found that TPC peaks are broad, almost always having a peak width at half height greater than 50° C. As a result, in the time domain the peak width is typically greater than 100 s. Therefore, the signal can be filtered on the seconds scale without significantly distorting it. A problem arises in that such filtering would greatly distort the calibration peaks. A novel approach is use different amounts of filtering for the two processes. A preferred embodiment of this invention uses low pass hardware filtering with a cutoff frequency of about 0.1 Hz. This will not significantly perturb calibration pulses, especially when a snubber is used. Software is also used to provide additional filtering which is based on the type of signal being acquired. In the case of a calibration pulse, averaging about 20 to 100 data points acquired over a time period of about 0.02 to 0.04 s is preferred. In the case of TPC, about 20 to 200 and preferably roughly 100 data points are averaged over about 0.04 to 0.2 s. In a preferred embodiment, each data bunch during TPC is taken at intervals of about 0.5 to 1° C., typically corresponding to roughly every 2 s. A moving average of adjacent data bunches is also done to further enhance the results.

A preferred embodiment of this invention allows TPC to be simultaneously done on multiple samples contained in different reactors. By clever arrangement of components and fluid pathways, a great savings in cost is achieved compared to using two independent TPC machines. The procedure is similar to that described for single TPC, but separate analyzers are used for each sample. A preferred analyzer is a TCD, in which case reaction gas from the tee is now directed through the reference side of each TCD, and a separate shunt from each reactor vent directs the effluent to the inlet side of the associated TCD. This procedure requires that the same reaction gas be used for each sample.

The unexpected flexibility of the present invention also provides for multiple simultaneous analyses during TPC and chemical reactions. In an alternative embodiment, a shunt connects a reactor vent to the inlet pert of the sample side of a TCD detector, and a second shunt connects the outlet pert of the sample side to a leak valve which provides a small leak of the reactor effluent into the vacuum manifold for analysis by mass spectrometry. This provides the unusual spectrometer to identify components. Once aware of the present disclosure, many other multiple ability to couple the highly quantitative response of the TCD with the ability of a mass methods can be constructed by persons skilled in the ad without undue experimentation.

The response of a mass spectrometer is highly dependent on a variety of parameters which are generally hard to control. In practice, almost all results of mass spectrometer analyses are described based on the raw output signal of the mass spectrometer. Especially in TPC of solid samples, it is sometimes desired to calculate results based on true mass or molar relationships. This is extremely tedious to do. In an alternative embodiment of the present invention, a computer acquires the signal from a mass spectrometer. The method is similar to that described for TPC with a TCD, but a D/A converter and more complex software is used which can control the scan of the mass spectrometer and acquire the data for each mass. A preferred D/A converter has 12 or 14 bit resolution and a full scale output of 5 or 10 V. The software also provides means for the user to input relative and absolute calibration factors for the masses being monitored. As a result, the raw data can now be converted to true mass and molar relationships.

The apparatus is contained in an enclosure of novel design, here termed partial double wall construction. In this construction appropriate components are mounted on an interior panel which is self supporting, inside of the main outer wall, and the mounted components are accessible to a user of the apparatus. By way of illustration, consider the case of a single inlet valve. Using the method of partial double wall construction, the valve is mounted on a very small self supporting panel. This small panel is placed just inside of the outer wall which in turn has a small hole to provide access to the valve. By this means, the apparatus is normally completely protected by its enclosure, the entire wall can be removed so as to enable nearly complete access to the interior of the apparatus, and the functionality of the apparatus is totally unaffected by the complete removal of the wall.

In another preferred embodiment of the present invention, TGA capability is added to the apparatus. The main components needed for a TGA subsystem are a microbalance and sample holder in a controlled atmosphere chamber, a furnace, and a device, preferably a computer, to record the output of the microbalance. The arrangement and operation of the components are well known to those skilled in the art of TGA. Gas flow from the main apparatus to the TGA subsystem is preferably via 1/16" to ¼" O.D. SS tubing. It is preferable to use a single gas line and connect one end to the bypass vent of the main apparatus. It is preferable that the sample chamber be evacuable, in which case it is preferably interfaced to the vacuum manifold by flexible SS bellows tubing of ½" to 1" I.D. and a shutoff valve to control evacuation. Electrical connections for temperature control and data acquisition are also made from the main apparatus. Use of the gas handling facilities, vacuum system, temperature control, and computer associated with the main machine greatly lowers the overall cost compared to a free standing TGA machine.

The process by which adsorption data is obtained and then treated can have a substantial effect on the speed and accuracy of chemisorption results. In a number of cases, from prior experience with a sample it is known that the chemisorption becomes constant above a pressure, Pmin. Therefore, if the experimental error is negligible with respect to curve fitting error, the chemisorption can be accurately obtained by acquiring a single data point of the amount of adsorption on each isotherm (V1 and V2, respectively) at P>Pmin. The chemisorption is then equal to V1 minus V2. Thus, a substantial saving in time results.

More generally, prior experience may show that each isotherm can be well approximated by an analytical function containing two adjustable constants. Common functions are the Freundlich and Langmuir isotherms. In this case, the curve is defined by acquiring only two data points for each isotherm and then fitting the curve to the data. The chemisorption is then equal to curve 1 minus curve 2. Thus, chemisorption as a function of pressure is obtained with a great savings in time.

For the most accurate chemisorption results, a clever process of removing most of the curve fitting error is used. Assuming that the experimental error is much less than the curve fitting error, then the amount of adsorption, Vi, experimentally measured at each pressure, Pi, can be considered to be exact even if the fitted curve does not pass through the data point. This enables a set of what is here defined as pseudo data points to be generated. For each value of Vi on the first isotherm, the corresponding pseudo data point is defined as Vi minus the value of V at the same pressure on curve 2. The process is partially depicted in FIG. 14 which shows one pseudo data point, 702 derived from the experimental data point 700 (the curve marked "refitted curve 2" is not used here). Similarly, for each value of Vi on the second isotherm, the corresponding pseudo data point is defined as the value of V at the same pressure on curve 1 minus Vi. The pseudo data points correspond to the chemisorption, and this data set can be fit to an analytical function to obtain the chemisorption as a function of pressure. Since the set of pseudo data points is about twice as large as the number of points on each isotherm and for each point all of the curve fitting error for one of the two data points used to generate the pseudo data point was removed, it is seen that this chemisorption curve will be more accurate than is obtained in the conventional manner.

Even higher accuracy can be achieved by a refinement in how the amount of adsorption for a pseudo data points is obtained from an isotherm. The improvement again makes use of the unexpected result that each experimental value of adsorption is more accurate than the fitted curve, but also makes use to the necessity to having a curve to properly interpolate data. It is here assumed that the isotherm has two adjustable parameters, but a similar methodology can be used for a curve with more adjustable constants. Most experimental pressures, Pi, on one isotherm will be bracketed by two data points taken at pressures Pa and Pb on the other isotherm such that Pa<Pi<Pb. Otherwise Pa and Pb are chosen to be closest in pressure to Pi. Only the corresponding Va and Vb are now used lot lilting to the previously determined curve. Therefore, the curve must pass through Va and Vb and almost all curve lilting error is removed from the pseudo data point Vi. The process is partially depicted in FIG. 14.

In a preferred embodiment of this invention software accomplishes the data treatment involved with using pseudo data points. In another preferred embodiment, the software also allows the user to specify a subset to the data points to be used for the curve lifting to achieve greater accuracy. In still another preferred embodiment, the software also allows the user to change some of the experimental data and parameters and then recalculates the results, thereby enabling analysis of errors. Suitable software can be readily provided by persons skilled in the art to programming without undue experimentation once aware of the present disclosure.

The principles, preferred embodiments, and methods of operation of the present invention have been described in the preceding specification. These descriptions are not meant to delineate all possible specifications, configurations of components, variations of components, materials of construction, modes of operation, or features of the machine. Many permutations of these items are possible and other components can be added lot the purpose to enabling other measurements while retaining the aforementioned novel multifunctional capabilities of the present invention. Variations and changes may be made by those skilled in the art without departing from the spirit of the present invention. In particular, there are many alternative choices of materials of construction for components which are in contact with reaction media, such as valves, tubing, and pressure transducers. In addition, there is a wide choice of packing materials and gaskets available for valves. Also, it has been noted that the pressure rating of the system can be increased to 3500 psi without any degradation in performance and maintaining the ability of full computer control. However, very few reactions are performed at pressures above 1500 psia. Pressures up to 10,000 psi can be achieved with the present invention, but at some loss in performance.

In order to give specific illustration of the nature of the invention and the manner of practicing it, the following working examples are described. However, it is to be fully understood that the invention is not limited to the specific measurements and details described in the examples.

In all of the following examples the apparatus is a preferred embodiment as described in connection with FIG. 2 and FIG. 8 through 14, unless stated otherwise. More particularly, the Gas Inlet System accommodates eight different reaction gases which include $O_2$, $N_2$, CO, $H_2$, and He, and a mass flow controller controls the rate Of flow of all reaction gases with the exception of $N_2$. A computer system was used for data analysis, to perform some of the TPC measurements, and to control the mass spectrometer.

EXAMPLE 1

A furnace was heated to 1000° C. and held at that temperature for >1 hr without the fan on so that the temperature of the internal parts of the furnace equilibrated. The temperature of the outer surface of the furnace was measured at the vertical midpoint of the furnace and at a point which is on the opposite side of the furnace from which the fan is located. The temperature was found to be 175° C., which is too hot to be easily handled. The fan was turned on and the temperature dropped to 85° C. With the Fast Air also on, the temperature dropped to 51° C. In another experiment, a furnace of 6" O.D. and having an annular air space adjacent to the outer shell was used. After equilibration of the furnace at 1000° C., the temperature of the shell was 120° C. An air flow reduced the temperature to 37° C. This Example shows the capability of the invention to use an external fan or internal air flow while heated to a high temperature to greatly lower the surface temperature of a furnace, thereby making it safer to use. This also allows the use of a furnace of much smaller diameter than expected and which therefore will have unusually fast thermal response.

EXAMPLE 2

The apparatus of Example 1 was used. A reactor of fused quartz was heated to 1100° C. The furnace was then automatically lowered and removed from the apparatus in 10 s. The reactor cooled to a temperature of 25° C. in 3 min. The furnace was reinstalled in 10 s. This Example demonstrates the ability of the invention to cool a reactor at an extremely fast rate.

EXAMPLE 3

The apparatus of Example 1 was used. A temperature controller was programmed to rapidly heat a furnace to 1000° C. A temperature of 1000° C. was achieved in 3.3 rain with no overshoot, corresponding to a heating rate of 303° C./min. This Example demonstrates the ability of the invention to heat to very high temperatures at an extremely fast rate and with good temperature control. The healing rate of a furnace of the same size and design but utilizing a conventional ceramic support for the heating element heated at 70° C./min. This Example and Example 2 also demonstrate the need for both using an annular space with air flow at high temperatures and an ultra light inner insulation in order to achieve exceptionally fast thermal response.

EXAMPLE 4

A furnace identical to that of Example 1 was used. The furnace was programmed to heat to 1000° C. and held at that temperature for 1 hr so that the temperature of the internal parts of the furnace equilibrated. The temperature controller was then turned off and the rate of cooling of the furnace measured in the absence of internal cooling air. The interior of the furnace cooled to 500° C. in 14 min, to 100° C. in 80 min, and to 35° C. in 145 min. This experiment shows the rate of cooling of the furnace without flowing a cooling gas inside of the furnace is relatively slow. A similar experiment was done except that Fast Air was directed to the interior (not annular space) in the furnace. The flow of air was about ⅓ the maximum amount which can be conveniently used by the apparatus. The interior of the furnace cooled to 500° C. in 1 min, to 100° C. in 4 min, and to 28° C. in 10 min. After cooling to 411° C. the cooling air was briefly turned off and the temperature rose to 532° C., indicating that the cooling is much higher in the interior region of the furnace which is directly exposed to the air flow. This Example shows that the invention can give very fast cooling of the interior of a furnace if a flow of cooling gas is directed to the interior of the furnace. Faster rates of cooling are expected with the use of a higher gas flow or the use of a cryogenic gas.

EXAMPLE 5

The apparatus of Example 1 was used. A furnace was heated to 1000° C. and held at that temperature for at least 1 hr so that the temperature of the internal parts of the furnace equilibrated. The furnace was then turned off and a flow of cooling air was started through the annular space of the furnace. The flow of air was approximately ⅓ the maximum amount which can be conveniently used by the apparatus. The interior of the furnace cooled to 500° C. in 6 min, to 100° C. in 27 min, and to 35° C. in 45 min. In a similar experiment the cooling air was briefly turned off after the interior of the furnace had cooled to 501° C. The temperature only rose to 518° C., indicating that the entire furnace was being cooled nearly uniformly by the air flow. This Example demonstrates that the invention can give rapid cooling of a complete furnace. Faster rates of cooling are expected with the use of a higher gas flow or the use of a cryogenic gas.

EXAMPLE 6

The apparatus of Example 1 was used. The Fast Air cooling line for a furnace was connected to a tank of $CO_2$ with a delivery pressure of 20 psig. The flow of cooling gas was about 1/5 the maximum amount which can be conveniently used by the machine and neither the regulator on the gas tank nor the tubing between the tank and furnace were insulated. Consequently, the experiment was not optimized for maximum cooling nor were the operating parameters of the temperature controller optimized. The furnace cooled to a temperature of −40° C. In a similar experiment, a flow of $CO_2$ was used to cool a furnace to −18° C. The furnace was then programmed to heat to 500° C. at a rate of 20° C./min. For setpoint temperatures above 62° C., the actual temperature of the furnace was <1° C. different from the setpoint temperature, and at lower temperatures the difference was no more than several degrees. This Example shows that the invention can be used to achieve subambient temperatures and subambient temperature programming with good temperature control. Lower temperatures can be achieved by the use of a higher gas flow or the use of $N_2$ gas.

EXAMPLE 7

The apparatus of Example 1 was used. A furnace was programmed to heat from 24° to 74° C. at 10° C./min. The operating parameters of the temperature controller were not optimized. The results are shown in the following table as Run #1. In a similar run, the Fast Air cooling line was simultaneously controlled by output 2 of the temperature controller. The results are shown in the following table as Run #2. This Example shows that the invention can achieve improved temperature control during temperature programming by the use of a controlled flow of a gas into the annular space of a furnace.

TABLE 1

| Run # | Ideal T (°C): | 24 | 34 | 44 | 54 | 64 | 74 |
|---|---|---|---|---|---|---|---|
| 1 | deviation (°C): | 0 | +11 | +23 | +21 | +17 | +7 |
| 2 | deviation (°C): | 0 | +6 | +7 | 0 | −2 | +3 |

EXAMPLE 8

The apparatus of Example 1 was used. The Vacuum Manifold was evacuated. The base pressure was $6 \times 10^{-9}$ torr. A 0.47 g sample of gamma alumina was put inside of a glass reactor and heated to 500° C. in flowing $H_2$ at 1 atm. The reactor was then evacuated in the roughing mode. It took about 1 s for the pressure in the Reaction Manifold to drop to 2 torr, which is low enough to safely switch to the high vacuum mode of evacuation. Upon switching, the the pressure in the Vacuum Manifold remained well below $10^{-2}$ torr which is safe for the ionization gauge and it took 20 s for the pressure in the Vacuum Manifold to drop to $1 \times 10^{-5}$ torr. This Example shows that the invention can achieve a very high vacuum and can pump down extremely fast.

EXAMPLE 9

The apparatus of Example 1 was used. The Gas Manifold, Reaction Manifold, and Low Pressure Transducer were evacuated and then isolated from the Vacuum Manifold. The total leak into the Gas Manifold, Reaction Manifold, and low pressure transducer was $2 \times 10^{-8}$ mL (STP)/s. In another experiment, the Gas Manifold, Reaction Manifold, and each of the eight lines for a reaction gas between the Gas Manifold and the redundant shutoff valves in the Gas Inlet System were pressurized to 1001 psia and then the redundant shutoff valves were closed. After 3 h there was no drop in pressure. This Example demonstrates that the invention can be constructed so as to have an extremely low leak level, both under high vacuum and at high pressure.

EXAMPLE 10

The apparatus of Example 1 was used. A 0.0295 g sample of 2.0% Co supported on gamma alumina was pretreated by heating to 1100° C. under vacuum. The surface area of the sample was determined in the conventional manner by measuring the adsorption of $N_2$ gas at 78K using the low pressure transducer to monitor the amount of adsorption. Data were entered into a computer program to calculate the results. An excellent BET plot resulted which yielded a surface area of 71.6 $m^2/g$ and a BET constant of 266. This Example demonstrates the ability of the invention to measure the surface area of a solid, to do so after pretreatment of a sample at very high temperature, and the ability to accurately measure the adsorption of a gas on a solid at very low temperature.

EXAMPLE 11

The apparatus of Example 1 was used. A 0.85 g sample of 0.05% Pd supported on gamma alumina was pretreated by heating to 450° C. in flowing $H_2$ followed by evacuation at this temperature. The dispersion of the catalyst was determined in the conventional manner by measuring the amount of $H_2$ chemisorption at 27° C. (defined as the difference in adsorption between two isotherms which are separated by evacuation of the sample at 27° C.). The dispersion of the sample was found to be 11.4%, corresponding to the chemisorption of 0.0051 mL (STP) of $H_2$. This Example demonstrates the ability of the invention to accurately measure the chemisorption of very small quantities of gas on a solid. The sensitivity of the apparatus for measuring the adsorption of a gas on a solid is found to be about 0.0002 mL STP, which is about 10-fold higher than any of the prior art devices.

EXAMPLE 12

The apparatus of Example 1 was used. A 0.501 g sample of 2% Co supported on gamma alumina was put in a SS reactor. A gas sampling valve was attached to a vent of the machine and plumbed so as to direct a sample of the reactor effluent to a gas chromatograph. The sample was pretreated by oxidation at 500° C. in a flow of $O_2$ and then reduction at 500° C. in a flow of $H_2$. A flow of CO and $H_2$ was then started through the reactor at 300° C. and a feed ratio of $H_2/CO=3$. The activity of the sample was determined for the hydrogenation of CO. The main product was found to be methane. The conversion was measured at pressures of 16, 150, 500, and 950 psia and at temperatures between 250° and 310° C. The activity of the catalyst declined during the measurements. Conventional analysis of the analytical data showed that the order of the reaction was with respect to the total pressure was about 1.0 and the activation energy of the reaction was about 80 kJ/mol. This Example shows that the invention can be used to run a reaction at high pressures, and that the invention can be used to determine many reaction parameters such as the conversion, products, catalyst lifetime, activation energy, and order of reaction.

EXAMPLE 13

A Gas Manifold and Vacuum Manifold very similar to that of Example 1 was connected with metal tubing to a TCD contained in a furnace equilibrated at about 50° C. A flow of 5% $H_2$ in Ar (as could be used in a temperature programmed reduction experiment) was divided into two streams. One stream flowed through the reference side of the TCD and the other steam flowed through the Gas Manifold and then through the sample side of the TCD. The TCD was allowed to equilibrate (defined as the drift of the output voltage being reduced to 0.02 mV in 10 min). The TCD was then turned off for 9 min (the gas flow continued) and then turned back on. It took 4 min for the TCD to stabilize. Therefore, equilibration time in excess of 4 min, defined as excess equilibration time, would be due to having to equilibrate a gas mixture flowing through the TCD. In a second experiment, the TCD was allowed to equilibrate in a gas flow of 5% $H_2$ in Ar and then the gas lines were purged with a mixture of 5% $O_2$ in He (as could be used in a successive temperature programmed oxidation experiment). The mixture of 5% $H_2$ in Ar was again flowed through the system and the TCD turned back on. The excess equilibration time was 72 min, being the time it took the $H_2$/Ar mixture to completely flush the $O_2$/He mixture from the gas lines. In a similar experiment, the mixture of 5% $O_2$ in He was removed by brief evacuation. The mixture of 5% $H_2$ in Ar was then again flowed through the system and the TCD turned back on. It was found that the excess equilibration time was only 9 min. This Example demonstrates that the invention can be used to evacuate the gas lines going to a detector, thereby achieving a much faster equilibration time than when flushing the gas from the lines.

EXAMPLE 14

A Gas Manifold and Vacuum Manifold very similar to that of Example 1 was connected to a SS reactor and the exit of the reactor was connected with metal tubing to a leak valve of a mass spectrometer (MS). A 0.1 g sample of Rh-Zn supported on silica (4% Rh by weight, Rh/Zn atomic ratio=3.3) was placed in the reactor and pretreated by reduction in flowing $H_2$ at 400° C. followed by evacuation and then cooling to 25° C. The amount of CO chemisorption was measured in the conventional manner at 25° C. and found to be 0.062 mL STP. Following the chemisorption of CO, a 21 mL/min flow of He was passed through the reactor and the leak valve adjusted so as to give a pressure in the MS of $5 \times 10^{-6}$ torr. The reactor was then heated from 30 to 400° C. at 20° C./min and the evolution of CO was measured by monitoring mass 28 with the MS. This type of experiment is termed temperature programmed desorption. The CO desorbed in a single peak with a peak height of $9.6 \times 10^{-8}$ A. The leak valve was then removed from the MS and the reactor was attached to the vacuum system of the MS using $\frac{1}{4}''$ O.D. metal tubing. The catalyst was then protreated as before and the CO chemisorption repeated, yielding the same result. A temperature programmed desorption experiment was now performed in which the desorbing CO was directly evacuated into the MS. The CO desorbed in a single peak with a peak maximum of $1.48 \times 10^{-5}$ A. This Example shows that the invention can be used to do temperature programmed desorption experiments with MS analysis in both the conventional mode in which the desorbing gas is swept out of the reactor by a carrier gas and is then bled into a MS as well as by an improved method involving direct evacuation into a MS. Further, the latter method yields about a 150-fold increase in sensitivity.

EXAMPLE 15

The apparatus of Example 1 was used. A temperature programmed desorption experiment was done with a sample of 2% Ru supported on alumina. The sample was exposed to a mixture of CO+$H_2$ at 25° C., the reactor evacuated, and then a 20 mL/min flow of He was passed through the reactor and to, a leak valve attached to a MS. The furnace was cooled with $CO_2$ and then the temperature was ramped from $-18°$ to 500° C. at 20° C./min. The desorption of $H_2$, CO, and $CH_4$ (formed by reaction between the first two gases) was measured by monitoring masses 2, 28, and 16, respectively, using a mass spectrometer. A large and broad CO peak was observed, but only very small amounts of $H_2$ and $CH_4$ were observed. This Example shows that the invention can can be used to do subambient temperature programmed desorption.

EXAMPLE 16

The apparatus of Example 1 was used. A 0.1007 g sample of 2% Mo supported on alumina was placed into a reactor of fused quartz. The sample was pretreated by oxidation at 600° C. in flowing $O_2$ followed by evacuation and then cooling to 25° C. This pretreatment converts the sample to $MoO_3$ supported on alumina. The vent of the reactor was attached to the sample side of a TCD. A 24 mL/min flow of 5% $H_2$ in Ar was then passed through the reference side of the TCD and a similar flow was passed through the reactor and then through the sample side of the TCD. The temperature of the furnace was then raised from 60 to 1200° C. at the rate of 20° C./min while the output of the TCD was monitored. When the $MoO_3$ gets reduced, $H_2$ is consumed from the flow of carrier gas and a peak is observed. This type of experiment is termed temperature programmed reduction. A small peak was observed near 580° C. and a large peak was observed near 950° C., corresponding to the reduction of $MoO_3$ to Mo metal. This Example shows that the invention can be used to do temperature programmed reduction experiments and can do them unusually high temperatures.

EXAMPLE 17

The apparatus of Example 1 was used for blank TPC runs using an empty reactor. A TCD was used. The output signal was acquired by a computer and displayed in real time, Software also provides for autoranging of the analog to digital converter to enhance resolution, noise rejection, signal averaging, numerous types of graphical display, automatic correction for various potential experimental errors such as changes in flow and temperature offsets, printing and storage of data, and calculation of various results including amount of gas reacted and changes in oxidation number of a solid. Multiple TPC curves can be displayed and manipulated simultaneously. In separate experiments carrier gases of He and of hydrogen in argon were used at flow rates of about 18 mL/min and heating rates of about 30° C./min. The temperature range was from ambient to about 1000° C. The typical baseline drift was 0.015 mV, being better than prior ad apparatus and more than 10-fold better than found with the Altamira AMI-1. It is believed that part of the improved performance is due to the extremely low leak of the present invention.

EXAMPLE 18

The apparatus of Example 1 was used to perform TPC in an automated manner similar to that described in Example 17. The sample was 0.5 g of alumina containing 0.1% Ru and 1.0% Mo in the oxide form. TPC was done at a flow rate of about 18 mL/min, a heating rate of 30° C., a temperature range of 30 to 100° C., and a detector current of about 80 mA. The carrier gas was 46% hydrogen in argon. Even at this low metal loading and high concentration of hydrogen, the peak for the reduction of the Ru oxide could be accurately measured due to the very low drift. This example shows that the present invention is more accurate than prior art apparatus and can readily do TPC at high concentrations of hydrogen.

EXAMPLE 19

The apparatus of Example 1 equipped with a remotely actuated GSV was used to measure the response of a TCD as a function of the mole percent hydrogen in an argon carder at a constant detector current of 80 mA. Data was acquired in an automated manner using the computer and software system described in Example 17. At 46% hydrogen, the response was 5.8-fold less than the response at 5% hydrogen. It is known that the sensitivity of a TCD increases about in proportion to the 2.5 power of the current. Based on the TCD manufacturer's specifications on how the maximum recommended current varies with the type of gas, it can be calculated that at 46% hydrogen the current could be increased about 60% over the value for pure argon. This effect alone would increase the sensitivity by a factor of about 3.2. Thus, by using 46% hydrogen and the increased current, the net loss in sensitivity is only 5.8/3.2=1.8. This example demonstrates that TPC can be done with high concentrations of hydrogen and only modest loss of sensitivity.

EXAMPLE 20

The apparatus of Example 1 was used to measure the chemisorption of CO on Fe supported on alumina. The catalyst weight was 0.5 g and the loading was 0.5% Fe. The volumetric dual isotherm process was used. Using the conventional method of extrapolating the data to zero pressure, the chemisorption was found to be 0.066 mL STP. The data is not well fit by a straight line. By using the pseudo data point method and several functions for curve fitting, it was found that the data are well fit by Freundlich isotherms. The chemisorption at 235 torr was found to be 0.170 cc STP. This example demonstrates that the pseudo data point method can greatly improve the accuracy of chemisorption data, shows that the use of multiple analytical functions to fit the isotherms improves the accuracy, and shows the use of assessing error by having software recalculate results using different processes.

What is claimed:

1. A process for performing temperature programmed characterization, comprising:
   providing an apparatus having a thermal conductivity detector having a reference side and a sample side, and a sample chamber containing a solid sample;
   passing a flow of gas through said reference side; and
   passing a flow of gas through said sample side wherein neither of the flows of gas passes through said sample chamber for a time sufficient to equilibrate said thermal conductivity detector;
   then terminating said flow of gas through said sample side and replacing it with a flow gas which passes through said sample chamber and then through said sample side; and,
   then performing temperature programmed characterization on said solid sample.

2. The process of claim 1 wherein said gas flow through said sample side of step one is achieved by directing the effluent from the reference side of said thermal conductivity detector into the sample side of said thermal conductivity detector.

3. The process of claim 1 which further comprises splitting a single flow of gas into two streams and directing one said stream into said reference side and directing the second said stream into said sample side.

4. A process for shortening the equilibration time of a thermal conductivity detector prior to performing thermal programmed characterization comprising: providing an apparatus comprising a gas supply of carrier gas, a sample chamber containing a solid sample, a thermal conductivity detector having a sample side and a reference side, and tubing connecting said sample chamber and said sample side;
   evacuating said tubing and said sample side or evacuating said sample chamber and said tubing and said sample side;
   then starting a constant flow of said carrier gas through said sample chamber, said tubing, and said sample side;
   and then performing temperature programmed characterization on said solid sample.

5. A process for shortening the equilibration time of a thermal conductivity detector prior to performing temperature programmed characterization comprising: providing an apparatus comprising a gas supply of carrier gas, a sample chamber containing a solid sample, a thermal conductivity detector having a sample side and a reference side, a mass flow controller upstream of said sample chamber operable to control a flow of said carrier gas into said sample chamber, tubing connecting said mass flow controller and said sample chamber;
   evacuating said tubing and said sample chamber or evacuating said mass flow controller and said tubing and said sample chamber;
   then starting a constant flow of said carrier gas through said mass flow controller, said tubing, said sample chamber, and said sample side;
   then performing temperature programmed characterization on said solid sample.

6. A process for shortening the equilibration time of a thermal conductivity detector prior to performing temperature programmed characterization comprising: providing an apparatus comprising a sample chamber containing a solid sample, a thermal conductivity detector having a sample side and a reference side, and said thermal conductivity detector to have an average current of i amps during temperature programmed characterization;
   setting the current to a value greater than i;
   then setting the current to the value i;
   then performing temperature programmed characterization on said solid sample with the thermal conductivity detector set at a current of i.

7. In a process for performing temperature programmed characterization of reactant including providing an apparatus comprising a sample chamber containing a solid sample, a gas supply of carrier gas, said carrier gas containing a first component which can react with said solid sample and a second component which is inert, a thermal conductivity detector having a sample side and a reference side, flowing said carrier gas through said chamber and then into said sample side measuring the thermal conductivity of the carrier gas; and determining adsorption and desorption characteristics of the first component with respect to the solid sample; the improvement comprising;
   said first component being present in a concentration greater than 25 mole percent and less than 95 mole percent of said carrier gas.

8. The process of claim 7, wherein said first component is hydrogen and said second component is argon.

9. The process of claim 7 wherein said first component is hydrogen and said second component is argon.

* * * * *